United States Patent
Rudick et al.

(10) Patent No.: US 9,968,642 B2
(45) Date of Patent: May 15, 2018

(54) COMPOSITIONS AND METHODS FOR TREATMENT OF PAIN

(71) Applicant: Northwestern University, Evanston, IL (US)

(72) Inventors: Charles N. Rudick, Chicago, IL (US); David J. Klumpp, Chicago, IL (US); Anthony J. Schaeffer, Hinsdale, IL (US)

(73) Assignee: Northwestern University, Evanston, IL (US)

( * ) Notice: Subject to any disclaimer, the term of this patent is extended or adjusted under 35 U.S.C. 154(b) by 0 days. days.

(21) Appl. No.: 14/567,751

(22) Filed: Dec. 11, 2014

(65) Prior Publication Data

US 2015/0320806 A1 Nov. 12, 2015

Related U.S. Application Data

(63) Continuation of application No. 13/416,500, filed on Mar. 9, 2012, now abandoned.

(60) Provisional application No. 61/450,937, filed on Mar. 9, 2011.

(51) Int. Cl.
*A61K 35/741* (2015.01)
*C12R 1/19* (2006.01)
*C12N 1/20* (2006.01)
*A61K 35/00* (2006.01)

(52) U.S. Cl.
CPC .............. *A61K 35/741* (2013.01); *C12R 1/19* (2013.01); *A61K 2035/115* (2013.01); *C12N 1/20* (2013.01)

(58) Field of Classification Search
None
See application file for complete search history.

(56) References Cited

U.S. PATENT DOCUMENTS

| | | | |
|---|---|---|---|
| 6,368,599 | B1 | 4/2002 | Langermann et al. |
| 6,479,051 | B1 | 11/2002 | Bruce et al. |
| 7,018,629 | B2 | 3/2006 | Jacob et al. |
| 2002/0044926 | A1 | 4/2002 | Reid et al. |
| 2008/0241226 | A1 | 10/2008 | Albein et al. |
| 2009/0041727 | A1 | 2/2009 | Suzuki et al. |

FOREIGN PATENT DOCUMENTS

WO 2010034479 A1 4/2010

OTHER PUBLICATIONS

Acosta & Davies, "Bacterial lipopolysaccharide regulates nociceptin expression in sensory neurons." J Neurosci Res. Apr. 2008; 86(5):1077-86.

Aksoy et al., "Protein kinase C epsilon: a new target to control inflammation and immune-mediated disorders." Int J Biochem Cell Biol. Feb. 2004; 36(2):183-8.

Andersson et al. "Persistence of *Escherichia coli* bacteriuria is not determined by bacterial adherence." Infect Immun. Sep. 1991; 59(9):2915-21.

Backhed et al., "TLR4-dependent recognition of lipopolysaccharide by epithelial cells requires sCD14." Cell Microbiol. Aug. 2002;4(8):493-501.

Broom et al., "Cyclooxygenase 2 expression in the spared nerve injury model of neuropathic pain." Neuroscience. 2004;124(4):891-900.

Fischer et al. "Mechanism of pathogen-specific TLR4 activation in the mucosa: fimbriae, recognition receptors and adaptor protein selection." Eur J Immunol. Feb. 2006;36(2):267-77.

Hagberg et al., "Difference in susceptibility to gram-negative urinary tract infection between C3H/HeJ and C3H/HeN mice." Infect Immun. Dec. 1984;46(3):839-44.

Hang et al., "Interleukin-8 receptor knockout mice have subepithelial neutrophil entrapment and renal scarring following acute pyelonephritis." J Infect Dis. Dec. 2000;182(6):1738-48.

Hedlund et al., "Type 1 fimbriae deliver an LPS- and TLR4-dependent activation signal to CD14-negative cells." Mol Microbiol. Feb. 2001;39(3):542-52.

Holthusen & Arndt, "Nitric oxide evokes pain at nociceptors of the paravascular tissue and veins in humans." J Physiol. Aug. 15, 1995;487 ( Pt 1):253-8.

Hultgren et al., "Chaperone-assisted assembly and molecular architecture of adhesive pili." Annu Rev Microbiol. 1991; 45:383-415.

Johnson et al. "Clonal and pathotypic analysis of archetypal *Escherichia coli* cystitis isolate NU14." J Infect Dis. Dec. 15, 2001;184(12):1556-65.

Kawai & Akira, "SnapShot: Pattern-recognition receptors." Cell. Jun. 1, 2007;129(5):1024.

Klumpp et al., "Uropathogenic *Escherichia coli* potentiates type 1 pilus-induced apoptosis by suppressing NF-kappaB." Infect Immun. Nov. 2001;69(11):6689-95.

Klumpp et al., "Dietary Sensitivity of Inerstitial Cystitis-Bane and Opportunity." European Urological Review 2009, 4(1):54-56.

Lindberg, "Asymptomatic bacteriuria in school girls. V. The clinical course and response to treatment." Acta Paediatr Scand. Sep. 1975;64(5):718-24.

Ma et al. "Role for both spinal cord COX-1 and COX-2 in maintenance of mechanical hypersensitivity following peripheral nerve injury." Brain Res. May 24, 2002; 937(1-2):94-9.

Numazaki et al., "Direct phosphorylation of capsaicin receptor VR1 by protein kinase Cepsilon and identification of two target serine residues." J Biol Chem. Apr. 19, 2002;277(16):13375-8.

Premkumar & Ahern, "Induction of vanilloid receptor channel activity by protein kinase C." Nature. Dec. 21-28, 2000;408(6815):985-90.

Ragnarsdottir et al., "Reduced toll-like receptor 4 expression in children with asymptomatic bacteriuria." J Infect Dis. Aug. 1, 2007;196(3):475-84.

Reeve et al., "Intrathecally administered endotoxin or cytokines produce allodynia, hyperalgesia and changes in spinal cord neuronal responses to nociceptive stimuli in the rat." Eur J Pain. 2000;4(3):247-57.

(Continued)

*Primary Examiner* — Jennifer Pitrak McDonald
*Assistant Examiner* — Qing Xu
(74) *Attorney, Agent, or Firm* — Casimir Jones, S.C.; Tanya Arenson

(57) ABSTRACT

The present invention provides compositions and methods for treatment or prevention of pain resulting from infection, infection related pain, and non-infectious pain as well as treatment or prevention of infections or adverse health consequences associated with infections.

10 Claims, 22 Drawing Sheets

(56) References Cited

OTHER PUBLICATIONS

Rhee & Hwang "Murine TOLL-like receptor 4 confers lipopolysaccharide responsiveness as determined by activation of NF kappa B and expression of the inducible cyclooxygenase." J Biol Chem. Nov. 3, 2000; 275(44):34035-40.

Roos et al., The Asymptomatic Bacteriuria *Escherichia coli* Strain 83972 Outcompetes Uropathogenic *E. coli* Strains in Human Urine. Infect. Immun. 2006, 74(1):615-624.

Rudick et al., "Mast cell-derived histamine mediates cystitis pain." PLoS One. May 7, 2008, 3(5):e2096.

Rudick et al., "Organ cross talk modulates pelvic pain." Am J Physiol Regul Integr Comp Physiol. Sep. 2007; 293(3):R1191-8.

Schilling et al., "CD14- and Toll-like receptor-dependent activation of bladder epithelial cells by lipopolysaccharide and type 1 piliated *Escherichia coli*." Infect Immun. Mar. 2003;71(3):1470-80.

Schilling et al., "Toll-like receptor 4 on stromal and hematopoietic cells mediates innate resistance to uropathogenic *Escherichia coli*." Proc Natl Acad Sci USA Apr. 1, 2003;100(7):4203-8.

Sokurenko et al., "Valency conversion in the type 1 fimbrial adhesin of *Escherichia coli*." Mol Microbiol. Aug. 2001;41(3):675-86.

Sturge, "The Phenomena of Angina Pectoris, and Their Bearing Upon the Theory of Counter-Irritation." Brain (1883) 5(4): 492-510.

Tanga et al., "The CNS role of Toll-like receptor 4 in innate neuroimmunity and painful neuropathy." Proc Natl Acad Sci U S A. Apr. 19, 2005;102(16):5856-61.

Wadachi & Hargreaves, "Trigeminal nociceptors express TLR-4 and CD14: a mechanism for pain due to infection." J Dent Res. Jan. 2006;85(1):49-53.

Mulvey et al., "Induction and Evasion of Host Defenses by Type 1Ð Piliated Uropathogenic *Escherichia coli*." Science 1998, 282:494-497.

Parvez et al., "Probiotics and their fermented food products are beneficial for health." J Applied Microbiology 2006, 100: 1171-1185.

Reid et al., "Oral probiotics can resolve urogentical infections." FEMS Immunology and Medical Microbiology 2001, 30: 49-52.

Rudick et al., "Host-Pathogen Interactions Mediating Pain of Urinary Tract Infection" J Infect Dis. Apr. 15, 2010; 201(8): 1240-1249.

Figure 6 Cont.
E
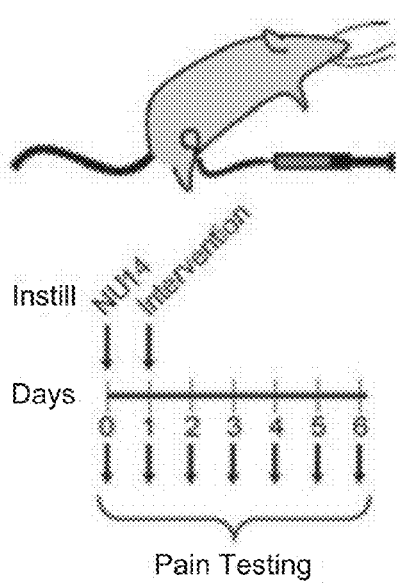
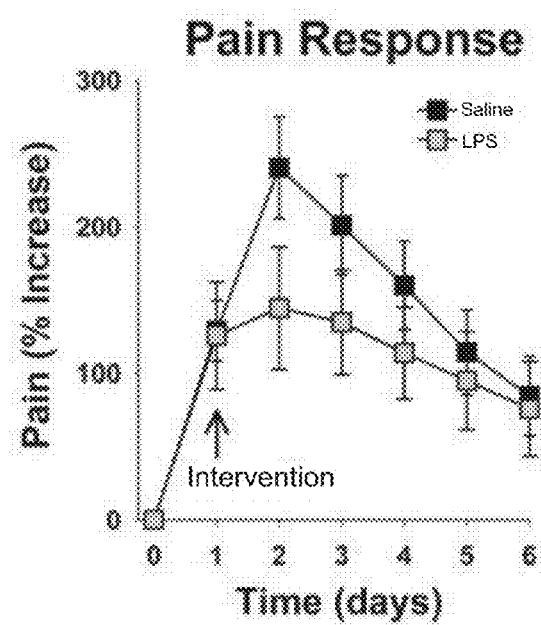

Figure 12
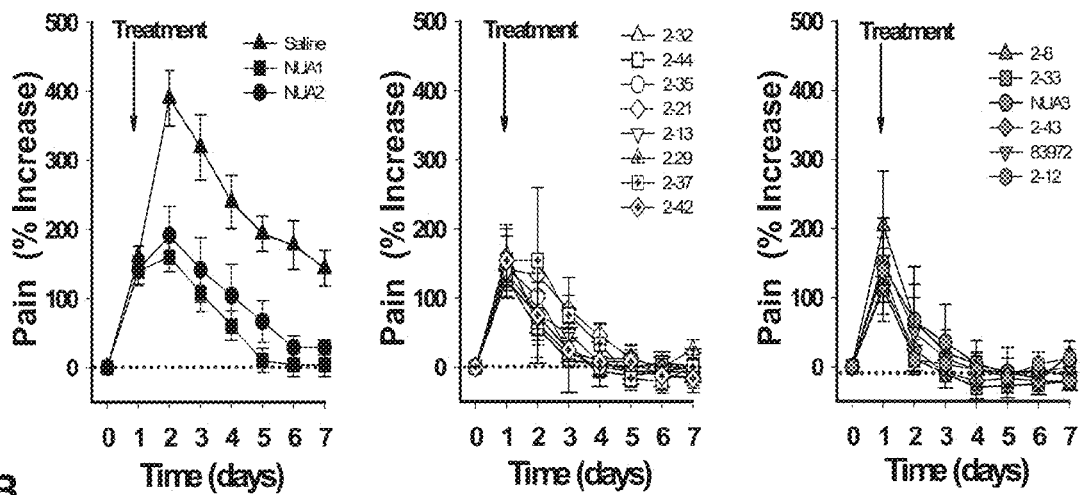
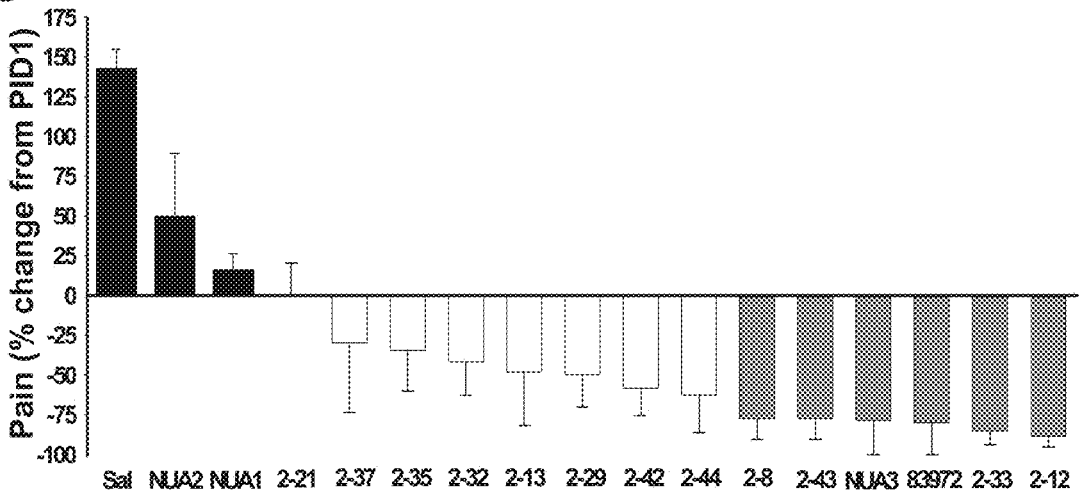
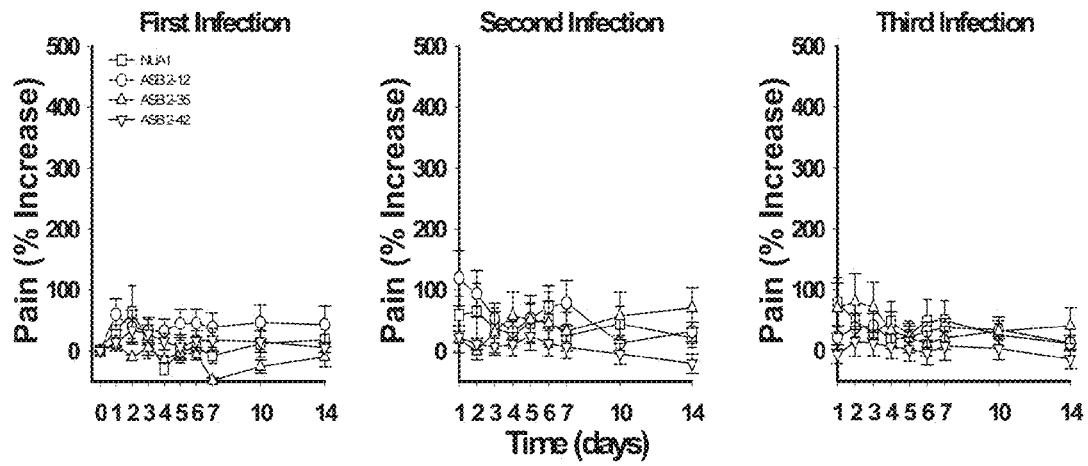

Figure 18
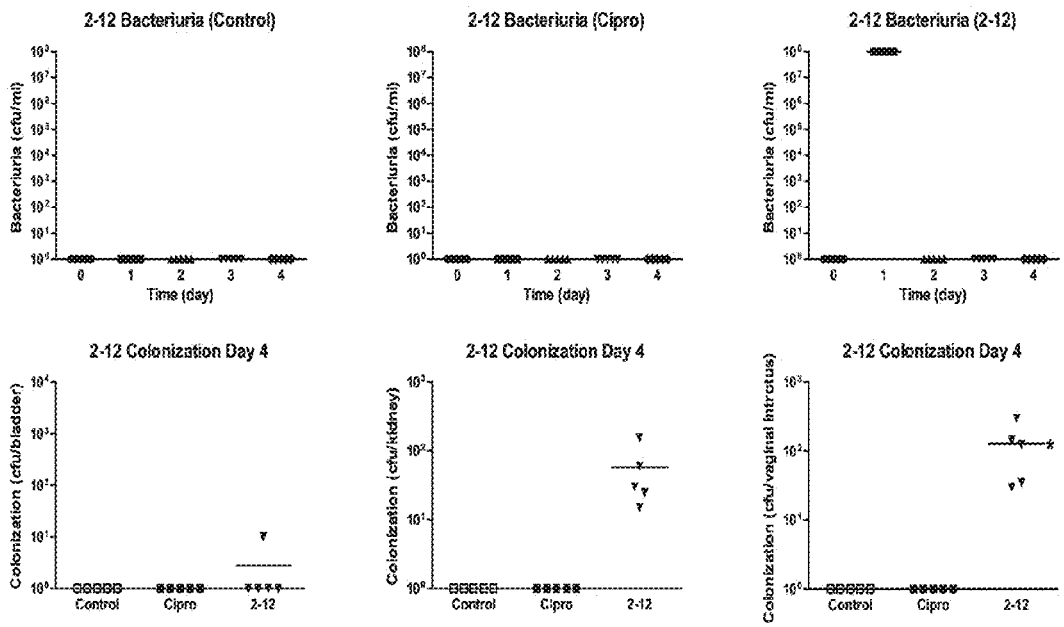
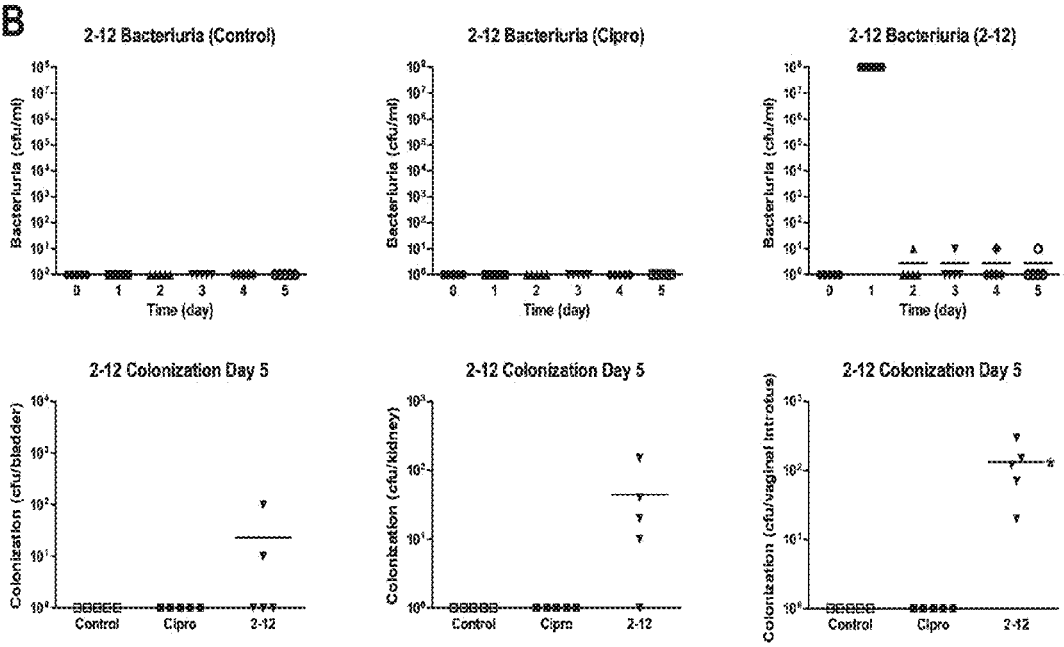

US 9,968,642 B2

COMPOSITIONS AND METHODS FOR TREATMENT OF PAIN

This application is a continuation of U.S. patent application Ser. No. 13/416,500, filed Mar. 9, 2012, which claims priority to U.S. Provisional Patent Application Ser. No. 61/450,937, filed Mar. 9, 2011, each of which are herein incorporated by reference in its entirety.

STATEMENT REGARDING FEDERALLY SPONSORED RESEARCH OR DEVELOPMENT

This invention was made with government support under grant numbers R01 DK066112 and T32 DK062716-05 by the National Institutes of Health. The government has certain rights in the invention.

FIELD OF THE INVENTION

The present invention provides compositions and methods for treatment or prevention of pain resulting from infection, infection related pain, and non-infectious pain as well as treatment or prevention of infections or adverse health consequences associated with infections.

BACKGROUND OF THE INVENTION

Urinary tract infection (UTI) is the second most common infectious disease that sends both men and women to seek treatment. In the United States, UTI accounts for >7 million office visits and >1 million emergency room visits, necessitating 100,000 hospitalizations annually (Schappert S M. Vital Health Stat 1997; 13:1-38; herein incorporated by reference in its entirety). Most community-acquired UTIs are due to infection by uropathogenic *Escherichia coli* (UPEC) that elicit an inflammatory response in the bladder during acute bacterial cystitis. Patients with UTI frequently have symptoms that include dysuria, voiding frequency or urgency, and pelvic pain. In contrast, ~5% of patients with UTI do not exhibit any of these symptoms and receive a diagnosis of asymptomatic bacteriuria (ASB) (Nicolle et al., Clin Infect Dis 2005; 40:643-654; herein incorporated by reference in its entirety). Although most patients with UTI experience pelvic pain, the mechanism underlying UTI-induced pelvic pain remains unknown.

UTIs are generally treated with antibiotics as a first line of treatment. Drugs most commonly recommended for simple UTIs include amoxicillin (Amoxil, Trimox), ciprofloxacin (Cipro), nitrofurantoin (Furadantin, Macrodantin), trimethoprim (Proloprim) and the antibiotic combination of trimethoprim and sulfamethoxazole (Bactrim, Septra). For severe UTIs, hospitalization and treatment with intravenous antibiotics may be necessary. However, many antibiotic resistant bacteria are present in the environment, especially in hospital and other health care settings. Thus, additional treatments for UTIs are needed.

SUMMARY OF THE INVENTION

The present invention provides compositions and methods for treatment or prevention of pain resulting from infection, infection related pain, and non-infectious pain as well as treatment or prevention of infections or adverse health consequences associated with infections.

In some embodiments, the present invention provides a method for treatment or prevention of pain comprising administering a probiotic composition to a subject having pain (e.g., pelvic pain). In some embodiments, the present invention provides a method for treatment or prevention of pain arising from infection (e.g., active or resolved UTI infection caused by *E. coli*), treatment of active infection (e.g., decrease in number of infectious organisms), treatment of infection related pain, treatment of non-infectious pain (e.g., chronic or acute non-infectious pain), or treatment of symptoms of an infection (e.g., non-pain symptom), comprising administering a probiotic composition.

In some embodiments, probiotic compositions comprise probiotic bacteria. In some embodiments, probiotic compositions comprise compositions derived from probiotic bacteria. In some embodiments, compositions are derived directly from probiotic bacteria (e.g., isolated and/or purified from bacteria). In some embodiments, compositions are derived indirectly from probiotic bacteria (e.g., synthetically or recombinantly produced compositions). In some embodiments, probiotic compositions comprise LPS. In some embodiments, probiotic compositions comprise peptides, carbohydrates, lipids, nucleic acids, and/or other organic molecules. In some embodiments, compositions comprise asymptomatic *E. coli* strains isolated from the human urinary tract include, but are not limited to, NUA2, NUA1, 2-21, 2-37, 2-35, 2-32, 2-13, 2-29, 2-42, 2-44, 2-8, 2-43, NUA3, 83972, 2-33 or 2-12. In some embodiments, probiotic bacteria comprise *E. coli* strain 83972, 2-12 or a bacteria or strain that produces a functionally equivalent reduction in pain.

In some embodiments, pain is treated or prevented through a TLR4-dependent pathway. In some embodiments, pain is treated or prevented through an inflammation-independent pathway. In some embodiments, a probiotic composition treats or prevents infection and/or inflammation (e.g., in addition to treating pain). In some embodiments, a probiotic composition treats or prevents pain without treating or preventing infection and/or inflammation. In some embodiments, a probiotic composition is administered as a tablet, capsule, pill, injection, cream, ointment, lotion, slave, balm, suppository, solution, elixir, syrup, suspension, cream, lozenge, paste or spray. In some embodiments, a probiotic composition is administered systemically. In some embodiments, a probiotic composition is administered locally to the region of infection and/or pain (e.g., vaginally). In some embodiments, a probiotic composition is administered such that pain in the affected region of infection and/or pain is treated via organ crosstalk or via corresponding dermatomes. In some embodiments, the present invention provides a composition that reduces pain resulting directly or indirectly from infections in a subject.

In some embodiments, the present invention provides a composition comprising a probiotic composition formulated for treating pain (e.g., pelvic pain related or unrelated to infection by pathogenic bacteria). In some embodiments, a probiotic composition comprises a probiotic bacteria. In some embodiments, a probiotic compositions comprises a composition derived from a probiotic bacteria. In some embodiments, compositions comprise asymptomatic *E. coli* strains isolated from the human urinary tract include, but are not limited to, NUA2, NUA1, 2-21, 2-37, 2-35, 2-32, 2-13, 2-29, 2-42, 2-44, 2-8, 2-43, NUA3, 83972, 2-33 or 2-12. In some embodiments, probiotic bacteria comprise *E. coli* strain 83972, 2-12 or a bacteria or strain that produces a functionally equivalent reduction in pain.

Additional embodiments are described herein.

DEFINITIONS

As used herein, the term "probiotic" refers to microorganisms that have beneficial effects to a subject they are administered to. A probiotic may be administered live. "Probiotic compositions" may refer to a probiotic organism, a portion thereof, or a composition derived from a probiotic organism.

As used herein, the term "asymptomatic E. coli strain isolated from the human urinary tract" refers to a bacteria (e.g., probiotic E. coli bacteria) present in the human urinary tract that does not cause pain or other symptoms of an infection. Examples of asymptomatic E. coli strains isolated from the human urinary tract include, but are not limited to, NUA2, NUA1, 2-21, 2-37, 2-35, 2-32, 2-13, 2-29, 2-42, 2-44, 2-8, 2-43, NUA3, 83972, 2-33 or 2-12.

As used herein, the term "pain related to infection" refers to any pain (e.g., pelvic pain) that is related to infection (e.g., infection by a pathogenic bacteria such as pathogenic E. coli). In some embodiments, pain is caused by an active bacterial infection (e.g., urinary tract infection). In other embodiments, pain related to infection is pain in an individual that has previously had a bacterial infection that has been treated (e.g., the subject does not have an active infection).

As used herein, the term "non-infectious pain" refers to pain that is not related to an active infection or is associated with a prior infection. In some embodiments, "non-infectious pain" is "chronic non-infectious pain" or "acute non-infectious pain." As used herein, the term "chronic non-infectious pain" refers to pain that persists for extended periods of time (e.g., days, weeks, months or years). In some embodiments, "chronic non-infectious pain" refers to chronic pain that has not responded to treatment (e.g., pain medicine or anti-infective agent treatments).

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

A "pharmaceutical composition" is intended to include the combination of an active agent with a carrier, inert or active, making the composition suitable for diagnostic or therapeutic use in vivo, in vivo or ex vivo.

As used herein, the term "pharmaceutically acceptable carrier" encompasses any of the standard pharmaceutical carriers, such as a phosphate buffered saline solution, water, and an emulsion, such as an oil/water or water/oil emulsion, and various types of wetting agents. The compositions also can include stabilizers and preservatives. For examples of carriers, stabilizers and adjuvants see Martin, Remington's Pharmaceutical Sciences, 15th Ed., Mack Publ. Co., Easton, Pa. (1975).

"Pharmaceutically acceptable salt" as used herein, relates to any pharmaceutically acceptable salt (acid or base) of a compound of the present invention, which, upon administration to a recipient, is capable of providing a compound of this invention or an active metabolite or residue thereof. As is known to those of skill in the art, "salts" of the compounds of the present invention may be derived from inorganic or organic acids and bases. Examples of acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds of the invention and their pharmaceutically acceptable acid.

As used herein, the term "nutraceutical," refers to a food substance or part of a food, which includes a fusion protein. Nutraceuticals can provide medical or health benefits, including the prevention, treatment, or cure of a disorder.

The term "sample" as used herein is used in its broadest sense. As used herein, the term "sample" is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "subject" refers to any animal (e.g., a mammal), including, but not limited to, humans, non-human primates, rodents, and the like, which is to be the recipient of compositions and methods that may be provided by the present invention. Typically, the terms "subject" and "patient" are used interchangeably herein in reference to a human subject.

DESCRIPTION OF THE FIGURES

FIG. 12 shows pain response with and without treatment with a variety of probiotic isolates. A and B. Pain response following treating with a variety of strains. C. Pain after first, second, or third infection.

FIG. 15A shows that 2-12 provides pain relief superior to Cipro. FIGS. 15B and C show that 2-12 has antimicrobial activity in urine (B) and vagina (C). Graphs in A-C show number of days versus pain (A), and cfu/ml (B-C). Graphs in D and E show colonization of different bladder or vagina by different bacteria.

FIGS. 16C, E and G show that 2-12 relieves pain of *Proteus, E faecalis* or *Klebsiella* UTI that is superior to Cipro. The graphs show pain level (E, G) or bacteria counts (F, H) over time.

FIG. 18 shows 2-12 colonization (Saline, Cipro, 2-12). A) CFT703 B) *Proteus*.

DETAILED DESCRIPTION OF THE INVENTION

Figure 1:
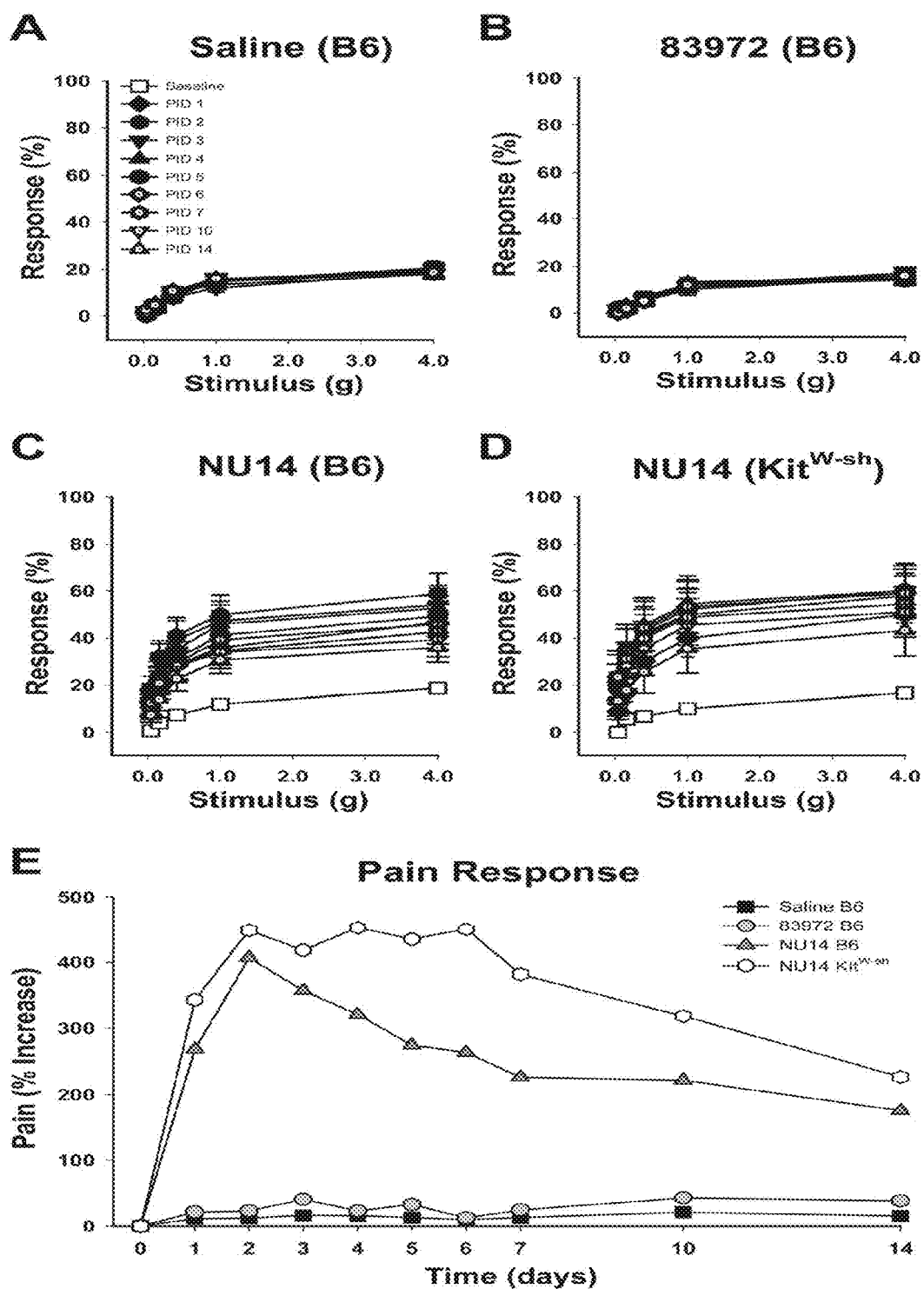
FIG. 1 shows graphs depicting NU14 inducing pelvic pain in female mice. Referred visceral hyperalgesia was measured as responses to mechanical stimulation of the pelvic region by using von Frey filaments of 5 calibrated forces. Data are reported as mean percentages of positive response±standard errors of the mean before instillation of bacteria (baseline) and at postinfection day (PID) 1, 2, 3, 4, 5, 6, 7, 10, and 14. A, Responses to pelvic stimulation of saline-infected female C57BL/6J mice (B6). B, Responses to pelvic stimulation of female B6 mice infected with 83972. C, Responses to pelvic stimulation of female B6 mice infected with NU14. D, Responses to pelvic stimulation of female $Kit^{W\_sh}/Kit^{W\_sh}$ mice infected with NU14. Analysis of variance indicated a significant increase in response frequency from baseline for all filaments tested in NU14-treated mice on days 1-10, with no significant differences in baseline between saline- and NU14-treated mice. NU14-treated mice exhibited a significant increase in response frequency from baseline in the largest 3 filaments only at day 14. E, Percentage responses for each day calculated as total responses to all fibers relative to baseline responses.

*E. coli* strain 2-12 was deposited with the American Type Culture Collection (ATCC), 10801 University Boulevard, Manassas, Va. USA on May 9, 2017 under Accession Number PTA-124177.

The present invention provides compositions and methods for treatment or prevention of pain resulting from infection, infection related pain, and non-infectious pain as well as treatment or prevention of infections or adverse health consequences associated with infections.

Uropathogenic *Escherichia coli* (UPEC) are responsible for the majority of uncomplicated urinary tract infections, which can present clinically as cystitis or pyelonephritis. Infection of the urinary tract by UPEC is associated with a robust innate immune response characterized by urothelial production of inflammatory chemokines and cytokines. Local production of inflammatory chemokines results in the rapid recruitment of neutrophils into the bladder lumen, which in turn mediate bacterial clearance (Schilling et al., *Escherichia coli*. Proc Natl Acad Sci USA 2003; 100:4203-4208; Hang et al., J Infect Dis 2000; 182:1738-1748 herein incorporated by reference in their entireties). The activation of the innate immune response in the urinary tract is dependent on pattern recognition of UPEC pathogen-associated molecular patterns by so-called pattern recognition receptors. UPEC pathogen-associated molecular patterns include lipopolysaccharide (LPS), flagella, type 1 pili, and pap pili (Zhang et al., Science 2004; 303:1522-1526; Hedlund et al., Mol Microbiol 2001; 39:542-552; herein incorporated by reference in their entireties), which can act through family members of pattern recognition receptors, including the Toll-like receptors (TLRs) and nucleotide binding and oligomerization domain-like receptors (Kawai et al., Cell 2007; 129:1024; herein incorporated by reference in its entirety).

The cystitis isolate NU14 is considered archetypal for UPEC and has been used to study many aspects of UTI pathogenesis (Johnson et al., J Infect Dis 2001; 184:1556-1565; herein incorporated by reference in its entirety). Several virulence factors have been characterized in UPEC, such as type 1 pili and LPS; the best-characterized UPEC virulence factor is the type 1 pilus, adhesive organelle (Hultgren et al., Annu Rev Microbiol 1991; 45:383-415; herein incorporated by reference in its entirety). Type 1 pili bind host urothelial cells by virtue of the FimH adhesin protein at the pilus tip, and FimH has lectin activity specific for mannosylated glycoproteins (Sokurenko et al., Mol Microbiol 2001; 41:675-686; herein incorporated by reference in its entirety). Instillation of the UPEC isolate NU14 induced rapid urothelial apoptosis that was abrogated after instillation of the isogenic ΔfimH mutant NU14-1, indicating a requirement for type 1 pili in the urothelial apoptotic response to UPEC infection (Mulvey et al., Science 1998; 282:494-497; Klumpp et al., Infect Immun 2001; 69:6689-6695; herein incorporated by reference in their entireties). LPS is also a common virulence factor and is a component of the gram-negative cell wall that binds to TLR4, initiating the innate response against UPEC. In culture, TLR4 signaling is required for nuclear factor KB activation and mediates LPS induction of urothelial interleukin (IL)-8 secretion by NU14 (Backhed et al., Cell Microbiol 2002; 4:493-501; Schilling et al., Infect Immun 2003; 71:1470-1480; herein incorporated by reference in their entireties). Despite this understanding of specific virulence factors in UTI pathogenesis, the mechanisms of UTI-associated pain are not understood.

Pain originating from a visceral organ is typically referred to a corresponding "dermatome" on the skin that shares common spinal cord innervation with the given visceral organ (Sturge, Brain 1883; 5:492-510, herein incorporated by reference in its entirety). This phenomenon has been used to show that bladder-induced pelvic pain is mast cell dependent and can be positively or negatively modulated by visceral organ cross-talk in a murine neurogenic cystitis model (Rudick et al., PLoS ONE 2008; 3:e2096; Rudick et al., Am J Physiol Regul Integr Comp Physiol 2007; 293: R1191-R1198, herein incorporated by reference in their entireties).

In experiments conducted during development of embodiments of the present invention, a murine urinary tract infection (UTI) model was used to compare pelvic pain behavior elicited by infection with uropathogenic *Escherichia coli* strain NU14 and ASB strains 83972 and 2-12. NU14-infected mice exhibited pelvic pain, whereas mice infected with 83972 did not exhibit pain, similar to patients infected with 83972 or 2-12. NU14-induced pain was not dependent on mast cells, not correlated with bacterial colonization or urinary neutrophils. UTI pain was not influenced by expression of type 1 pili, the bacterial adhesive appendages that induce urothelial apoptosis. However, purified NU14 lipopolysaccharide (LPS) induced Toll-like receptor 4 (TLR4)-dependent pain, whereas 83972 LPS induced no pain. Indeed, 83972 LPS attenuated the pain of NU14 infection, suggesting therapeutic potential. These data indicate a mechanism of infection-associated pain that is dependent on TLR4, yet independent of inflammation. These findings also indicate probiotic therapies that minimize the symptoms of infection without reliance on therapies that contribute to antimicrobial resistance.

Mast cell-deficient mice infected with NU14 develop the same magnitude of pelvic pain as infected wild-type mice, suggesting that UTI pelvic pain develops independent of mast cells. Pelvic pain in the neurogenic cystitis is dependent on mast cell-derived histamine and is transduced by histamine receptors 1 and 2 (Rudick et al, 2008, supra; incorporated herein by reference in its entirety). In contrast, pelvic pain induced in murine UTI originates from bacterial LPS that is transduced by TLR4. Therefore, the differential role of mast cells in cystitis models may be due to the nature of the initiating insult, which neurogenic cystitis is initiated in the central nervous system, whereas UTI in the peripheral nervous system. The present invention is not limited to any particular mechanism of action and an understanding of the mechanism of action is not necessary to practice the present invention.

Figure 4:
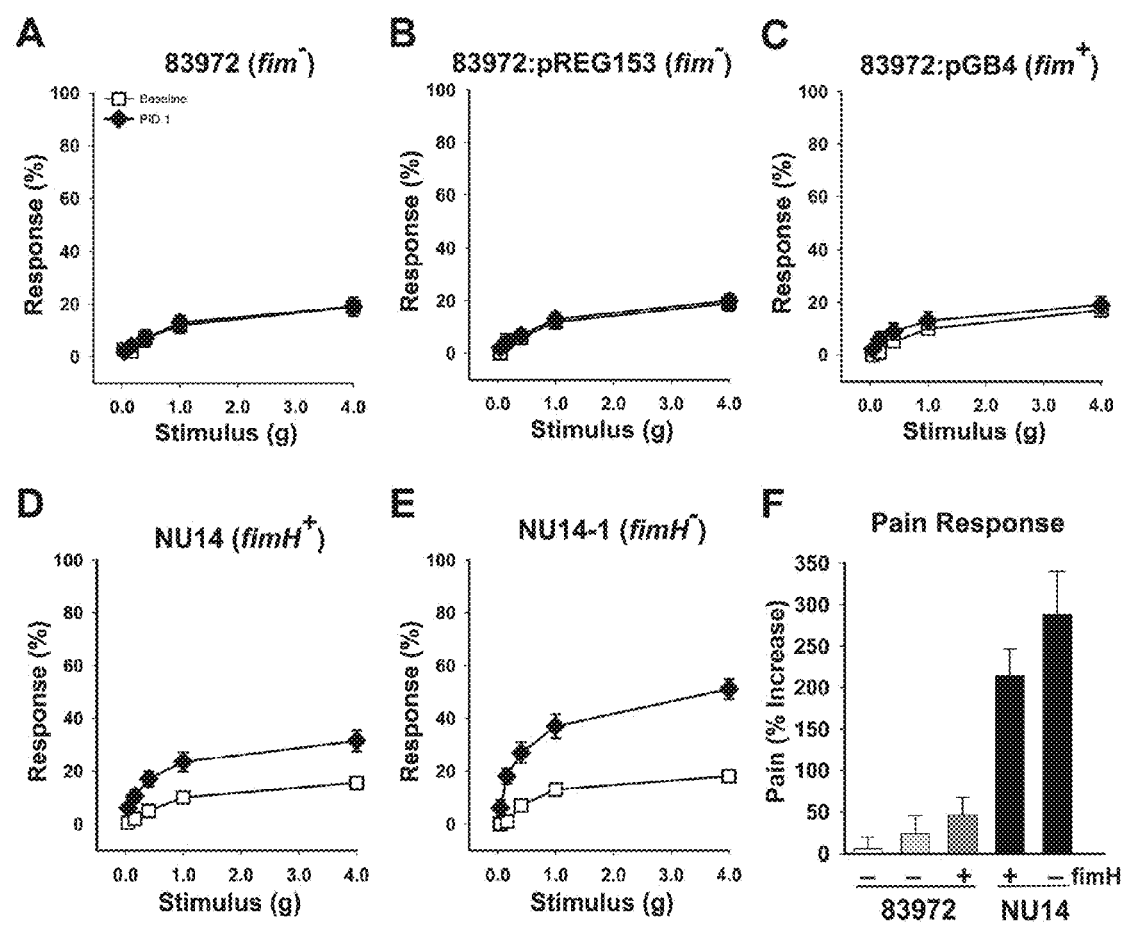
FIG. 4 shows graphs demonstrating that Type 1 pilus status does not influence urinary tract infection (UTI)-associated pelvic pain. Referred visceral hyperalgesia was measured as responses to mechanical stimulation of the pelvic region by von Frey filaments of 5 intensities. Responsiveness was characterized at baseline and 24 h after bacterial infection. A, Responses to pelvic stimulation of female B6 mice infected with 83972 without the fimB-fimD gene cluster (no type 1 pili). B, Responses to pelvic stimulation of female B6 mice infected with 83972:pREG153 without the fimB-fimD gene cluster (no type 1 pili). C, Responses to pelvic stimulation of female wild-type mice infected with 83972:pGB4 with the fimB-fimD gene cluster (expresses type 1 pili). D, Responses to pelvic stimulation of wild-type mice infected with NU14 with fimH (expresses type 1 pili). E, Responses to pelvic stimulation of wild-type mice infected with NU14-1 without fimH (greatly reduced expression of type 1 pili). F, Percentage responses 24 h after infection were calculated as total responses to all fibers relative to baseline responses for 83972 (white bar), 83972:pREG153 (light gray bar), 83972:pGB4 (dark gray bar), and NU14 with or without fimH (black bars).

Mast cells play roles in bladder pathophysiology that are separable from bladder-associated pain, and experiments conducted during development of embodiments of the present invention indicate similarly separable host responses induced by UPEC infection. NU14 induced pelvic pain behavior in mice that was not observed after infection with the ASB strain 83972, thus recapitulating human behavioral responses to UPEC and ASB strains (Andersson et al., Infect Immun 1991; 59:2915-2921; Lindberg U. Acta Paediatr Scand 1975; 64:718-724; incorporated herein by reference in their entireties). FimH induces rapid urothelial apoptosis and formation of urothelial lesions, indicating that FimH bladder pathology mediates pain. However, no relationship was identified between type 1 pilus expression and pain behavior, for either NU14 or 83972 (FIG. 4). Inflammation is often assumed to underlie infection pain, but a consistent relationship between pain and inflammation was not observed in experiments conducted during development of embodiments of the present invention. Pain did decay over time as urinary MPO decayed, but both whole bacteria and LPS purified from NU14 and 83972 induced similar inflammatory responses in vitro and in vivo. This is consistent with clinical findings that patients with ASB, who lack pain by definition, nonetheless often have pyuria (Schaeffer et al., supra; Nicolle et al., supra). Thus, the inflammation of cystitis is not sufficient by itself to mediate the pain of cystitis. Although LPS mediates cystitis pain through TLR4, the effects on pain appear independent of inflammatory actions.

Experiments conducted during development of embodiments of the present invention demonstrate that LPS mediates pelvic pain behavior. NU14 LPS confers a smooth colony morphology, whereas 83972 exhibits the rough phenotype, together suggesting that O antigen mediates the pain response. However, ECOR reference strain 71 is an ASB strain with O78 serotype, indicating that O antigen alone is insufficient to endow a strain with a pain-causing phenotype.

Experiments conducted during development of embodiments of the present invention demonstrate that LPS isolated from NU14 induced pelvic pain through a TLR4-dependent mechanism, providing a novel pathway of pelvic pain induction and relief. C3H-OuJ and C3H-HeJ are co-isogenic mouse strains, making them ideal for studying LPS-induced TLR4 signaling. Over time, the C3H-HeJ strain developed a spontaneous mutation in the TLR4 gene, rendering these mice defective in TLR4 signaling (35, incorporated herein by reference in its entirety). Although TLR4 involvement is well documented for bacterial defense, it has only recently been implicated in nociception. TLR4 signaling is important in patients with ASB and animal models (Ragnarsdottir et al., J Infect Dis 2007; 196:475-484; Hagberg et al., Infect Immun 1984; 46:839-844; Fischer et al., Eur J Immunol 2006; 36:267-27737-39, incorporated herein by reference in their entireties). Ragnarsdottir et al. (supra) report lower neutrophil TLR4 expression levels in patients with ASB that correspond with elevated levels of the TRIF adaptor protein and reduced levels of the TLR4 inhibitor SIGIRR. Experiments conducted during development of embodiments of the present invention collectively demonstrate a role for TLR4 in UTI-induced pelvic pain.

Although the present invention is not limited to any particular mechanism of action and an understanding of the mechanism of action is not necessary to practice the present invention, it is contemplated that LPS triggers UTI pain peripherally or centrally. TLR4 has been implicated in neuropathic pain because activation of microglial TLR4 leads to nuclear factor KB-dependent cyclooxygenase 2 up-regulation that contributes to central sensitization in peripheral injury models (Tanga et al., Proc Natl Acad Sci USA 2005; 102:5856-5861; Rhee et al., J Biol Chem 2000; 275:34035-34040; Ma et al., Brain Res 2002; 937:94-99; Broom et al., Neuroscience 2004; 124:891-900; incorporated herein by reference in their entireties). Likewise, intrathecal LPS induces enhanced dorsal horn neuronal firing that correlates with allodynia and hyperalgesia (Reeve et al., Eur J Pain 2000; 4:247-257; incorporated herein by reference in its entirety). Alternatively, TLR4 could mediate pain peripherally, either through sensory nerves or via the urothelium itself. Nociceptors have recently been shown to express TLR4, which could then lead to LPS-induced firing due to TLR-induced protein kinase C activation (Wadachi et al., J Dent Res 2006; 85:49-53; Acosta et al., J Neurosci Res 2008; 86:1077-1086; Aksoy et al., Int J Biochem Cell Biol 2004; 36:183-188; Numazaki et al., J Biol Chem 2002; 277:13375-13378; Premkumar et al., Nature 2000; 408:985-990; incorporated herein by reference in their entireties). Finally, urothelial TLR4 could mediate pain responses indirectly, by stimulating urothelial production of reactive oxygen species that can then activate peripheral nociceptors (Holthusen et al., J Physiol 1995; 487(Pt 1):253-258; incorporated herein by reference in its entirety). The involvement of TLR4 identifies a therapeutic target for managing UTIs. The present invention is not limited to any particular mechanism of action and an understanding of the mechanism of action is not necessary to practice the present invention.

Current UTI treatment practice employs empirical use of antimicrobials to eradicate acute infection, although the clinical condition of ASB already indicates that bladder infection is not necessarily deleterious in itself. Moreover, experimental infection of human subjects demonstrated that UTI was resolved naturally, over the course of several days, in the absence of intervention with antimicrobials (Wullt et al. Infect Dis Clin North Am 2003; 17:279-301 incorporated herein by reference in its entirety). Together, these observations provide an alternative therapeutic strategy for UTIs: treat the symptoms that drive patients to visit their physicians: pain and discomfort. Experiments conducted during development of embodiments of the present invention demonstrate that LPS purified from 83972 or 2-12 attenuated pelvic pain during NU14 infection (FIGS. 6E and 10-19). Data indicate that 83972—or LPS derived from an ASB strain—suppress UTI pain by interfering with TLR4-dependent pain induced by UPEC, thereby providing a novel treatment strategy using a probiotic that would minimize the symptoms of infection without reliance on empirical therapies that contribute to antimicrobial resistance.

Accordingly, in some embodiments, the present invention provides compositions and methods for treating pain (e.g., pain related to UTI) (e.g., TLR4-dependennt pain). In some embodiments, compositions and method comprise compositions (e.g., probiotics or compositions derived therefrom, LPS, LTA, etc.) or administration of such compositions to a subject for the treatment of pain (e.g., pelvic pain) (e.g., TLR4-dependent) pain. In some embodiments, the present invention provides probiotics (e.g., E. coli strain 83972 or 2-12, related strains, functionally equivalent strains, etc.) for the treatment of infection-related pain. In some embodiments, the present invention provides administration of compositions derived from, or related to probiotics (e.g., membrane fractions, LPS, functional derivatives of LPS such as mimetics, LTA, proteins, peptides etc.) for the treatment or prevention of infection (e.g., pain, inflammation, antimicrobial treatment, etc.). In some embodiments, the present invention provides treatment or prevention of pain that is inflammation-independent. In some embodiments, the present invention provides administration of LPS, LTA, or other compositions derived (e.g., directly or indirectly (e.g., produced recombinantly, synthetically produced) from probiotic organisms for the treatment of infection and/or pain.

In some embodiments, a treated subject does not have an infection at the time of treatment. In some embodiments, the subject does not have a urinary tract infection, a lower urinary tract infection, and/or a recurrent lower urinary tract infection. In some embodiments, the subject does not have a history of recurrent lower urinary tract infection, even if no infection is present at the time or treatment. In some embodiments, the subject does not suffer from incomplete bladder emptying. Likewise, in some embodiments, methods herein are not employed for the treatment or prevention of such infections or signs or symptoms.

In some embodiments, the present invention provides compositions and methods for treatment for non-infectious pain (e.g., pain in individuals with no active infection or no history of active infection). In some embodiments, the present invention provides compositions and methods for treatment of chronic non-infectious pain.

In some embodiments, the present invention provides bacteria or other pathogens, microbes, infectious agents, etc. which provide treatment or prevention of pain or non-infectious pain. The present invention is not limited to a particular bacterial strain. In some embodiments, the strain is an asymptomatic *E. coli* strain isolated from the human urinary tract (e.g., NUA2, NUA1, 2-21, 2-37, 2-35, 2-32, 2-13, 2-29, 2-42, 2-44, 2-8, 2-43, NUA3, 83972, 2-33 or 2-12; See e.g., FIG. 12). Asymptomatic *E. coli* strains isolated from the human urinary tract can be obtained, for example, from the *E. coli* Reference Center, Wiley Laboratory, Wiley Lane, The Pennsylvania State University.

In some embodiments, the present invention provides *E. coli* strain 83972, 2-12, or other functional similar or equivalent strains of *E. coli* or other bacteria that provide similar treatment or prevention of pain. In some embodiments, the present invention provides *E. coli* strains (e.g., 83972, 2-12, or related strains). In some embodiments, the present invention provides Enterobacteriaceae, Enterobacteriales, Gammaproteobacteria, Proteobacteria, Gram-negative bacteria, gram-positive bacteria (e.g., *streptococcus* species such as *S. milleri*), LPS-producing bacteria, LTA-producing bacteria, bacteria, microbes, and/or microorganisms capable of treating or preventing pain (e.g., pain arising from infection).

In some embodiments, the present invention provides compositions containing the bacterial strains described herein (e.g., 83972, 2-12 or related strains), bacterial products (e.g., LPS, peptides, LTA, etc.) derived (e.g., directly or indirectly) or obtained from the above bacteria and microorganisms. In some embodiments, compositions are pharmaceutical compositions comprising the active agent (e.g., the bacterial strains described herein) and one or more pharmaceutically acceptable carriers. In some embodiments, active agents (e.g., the bacterial strains described herein) are provided as a component of a nutraceutical, food or food product or as a food additive.

Those skilled in the art will appreciate that the compositions disclosed herein can be readily formulated to include additional compounds common in the pharmaceutical arts such as, excipients, extenders, preservatives, and bulking agents depending on the intended use of a composition. Furthermore, ingestible formulations of these compositions may also comprise any material approved by the United States Department of Agriculture (USDA) for incorporation into food products such as substances that are generally recognized as safe (GRAS) including, food additives, flavorings, colorings, vitamins, minerals, and phytonutrients. The term phytonutrients as used herein, refers to organic compounds isolated from plants having biological effects including, but not limited to, compounds from the following classes of molecules: isoflavonoids, oligomeric proanthcyanidins, indol-3-carbinol, sulforaphone, fibrous ligands, plant phytosterols, ferulic acid, anthocyanocides, triterpenes, omega 3/6 fatty acids, polyacetylene, quinones, terpenes, cathechins, gallates, and quercitin.

In some embodiments, the present invention provides treatment or prevention of TLR4-dependent pain. However, the present invention is not limited to pain produced by any particular target or pathway, and an understanding of the mechanism of the present invention is not required to practice methods described herein. In some embodiments, the present invention treats and/or prevents pain, inflammation, and/or infection by targeting TLR4-dependant or other pathways. In some embodiments, pain, inflammation, and/or infection are treated and/or prevented by targeting pathways not involving TLR4. In some embodiments, compositions and methods of the present invention provide a wide range of benefits. In some embodiments, compositions and methods induce a beneficial inflammatory response. In some embodiments, beneficial results (e.g., antimicrobial, pain reduction, etc.) are obtained without induction of an inflammatory response. In some embodiments, the present invention provides modulation of inflammatory response.

The present invention is illustrated for the treatment of pelvic pain (e.g., related or unrelated to UTI). However, the present invention is not limited to the treatment of pelvic pain. The compositions and methods of embodiments of the present invention find use in the treatment of a variety of infections (e.g., reduction in count of infectious agent), treatment of symptoms of an infection (e.g., pain or non-pain symptoms), infection related pain, and non-infectious pain. Examples include, but are not limited to, pain of the urogenital and GI tracts (e.g., vulvodynia, interstitial cystitis/painful bladder syndrome, urinary tract infection, bladder infection, urethral infection, prostate infection, and irritable bowel syndrome), back pain, migraine, otitis, sinusitis, orchitis, epididymitis, specific bacterial infections (e.g., stomach ulcers, gastritis), ear infections (e.g., chronic ear infections), *chlamydia*, mastitis, endometritis, Gonococcal infections, etc. In some embodiments, the present invention provides treatment, prevention or symptom reduction of infections caused by *Staphylococcus, Streptococcus, Clostridium, Bacillus, Erysipelothrix rhusiopathae, Listeria monocytogenes, Arcanobacterium pyogenes, Actinomyces, Nocardia, Mycobacterium, Enterobacteria, Enterobacteria, Salmonella, Escheria coli, Yersinia, Klebsiella, Shigella, Pseudomonas, Bordatella, Lawsonia intracellularis, Helicobacter, Spirochaetes, Borrelia, Chlamydia, Mycoplasma, Candida albicans*, etc. In some embodiments, the present invention provides treatment, prevention, and/or symptom reduction (e.g., pain or inflammation reduction) of infections of the bladder, kidney, urinary tract, vagina, genitals, urethra, digestive tract, respiratory system, ears, nose, nasal passages, sinus, oral cavity, oral-facial pain related to oral cavity, eye, etc.

EXPERIMENTAL

The following examples are provided in order to demonstrate and further illustrate certain preferred embodiments and aspects of the present invention and are not to be construed as limiting the scope thereof.

Example 1

Compositions and Methods

Animals.

Adult female mice (C57BL/6J, C3H-HeOuJ, or C3H-HeJ; 10-14 weeks old) were purchased from Jackson Laboratory. Mast cell-deficient $Kit^{W\_sh}/Kit^{W\_sh}$ mice (B6.Cg-$Kit^{W\_sh/HNihrJaeBsmJ}$; 10-14 weeks old) were maintained in facilities (17, herein incorporated by reference in its entirety). All experiments were performed using protocols approved by the Northwestern University Animal Care and Use Committee.

UPEC and ASB Strains.

NU14 is a clinical isolate of *E. coli* originally obtained from the urine of a patient with cystitis (Table 1) and is considered archetypal for UPEC (13, herein incorporated by reference in its entirety). NU14-1 is the corresponding fimH mutant that does not express type 1 pili (21, herein incorporated by reference in its entirety). ASB strain 83972 was isolated from a young Swedish girl who was infected for at least 3 years without symptoms (19, 20, herein incorporated by reference in their entireties) and is one of the most extensively characterized ASB strains (22, 23, herein incorporated by reference in their entireties).

TABLE 1

*Escherichia coli* Strains

| Strain | Characteristics | MSHA response | Reference |
| --- | --- | --- | --- |
| NU14 | B2 cystitis isolate | Positive | [21] |
| NU14-1 | NU14 with insertional disruption of fimH | Negative | [21] |
| 83972 | Asymptomatic bacteriuria isolate | Negative | [19] |
| 83972:pREG153 | 83972 with vector plasmid pREG153 | Negative | [22] |
| 83972:pGB4 | 83972 with fim plasmid pGB4 | Positive | [22] |

NOTE.
MSHA, mannose-sensitive hemagglutination.

Infection.

Female mice were anesthetized with isoflurane and instilled via transurethral catheter with a volume of 10 μL containing $1 \times 10^8$ colony-forming units of either NU14 or 83972 bacteria. After infection, bladders were harvested, homogenized, and plated on eosin methylene blue agar for colonization (24, herein incorporated by reference in their entireties). Urine was prepared according to manufacturer's recommendations and assayed for neutrophil myeloperoxidase (MPO) by enzyme-linked immunosorbent assay (Hycult Biosciences). Mice were tested before bacterial infection (baseline) and for up to 14 days after infection. Referred hyperalgesia and tactile allodynia were tested, as described elsewhere (17, 18, herein incorporated by reference in their entireties), using von Frey filaments applied to the abdomen (17, 18, 25, herein incorporated by reference in their entireties) and the plantar region of the hind paw (17, 18, 25, herein incorporated by reference in their entireties).

Purification of LPS.

LPS was isolated from *E. coli* strains NU14 and 83972 grown overnight on Luria-Bertani agar plates. Cultures were collected by swabbing, suspended in phosphate-buffered saline, and collected by centrifugation. LPS was then isolated using the LPS Extraction Kit (iNtRON Biotechnology), according to the manufacturer's recommended protocol. Preparations were then further purified to remove any contaminants that could activate additional members of the TLR pathway (26 herein incorporated by reference in its entirety); this process included ethanol precipitation, digestion with DNase I and RNase, and digestion with proteinase K, followed by a final ethanol precipitation. The concentration of LPS in each sample was determined with the Purpald assay, by measuring 2-keto-3-deoxyoctonate (KDO) levels and comparing them to a KDO standard curve (27, herein incorporated by reference in its entirety).

LPS Instillation.

NU14 or 83972 LPS (2.0 m/25 μl) was instilled via transurethral catheter into the bladder while isoflurane anesthesia was maintained. All mice were tested for referred hyperalgesia with von Frey filaments, before and 1, 4, 24, 48, 72, and 96 h after LPS instillation.

Lidocaine Treatment.

Lidocaine drug therapy was administered as a 2% lidocaine solution in water that was instilled into the colon via a Hamilton syringe catheter (18, herein incorporated by reference in its entirety).

Macrophage Responses to LPS.

Splenic macrophages were isolated from 8-10-week-old mice using CD11b MACS in conjunction with MACS LS magnetic columns (Miltenyi); the obtained purity was ~85%. Purified splenic macrophages were cultured under standard conditions in the presence of 100 ng/mL 83972 or NU14 LPS for 4 or 8 h. After incubation, supernatants were collected for quantifying secreted IL-6 by enzyme-linked immunosorbent assay (R&D Systems), and LPS-stimulated cells were immediately analyzed by flow cytometry. Flow cytometry was performed by staining for the following antibodies: allophycocyanin-anti-CD80 or biotin anti-CD86 and streptavidin-conjugated phycoerythrin-indotricarbocyanine (eBioscience), phycoerythrin-CD11b, and anti-CD16-CD32; hamster IgG and rat IgG2a,κ were used as isotype controls (BD PharMingen). Stained cells were analyzed on a FACSCanto flow cytometer (Becton Dickinson) with FACSDiva acquisition and FlowJo analysis software, version 8.7.3 (Tree Star).

Statistical Analyses.

Results were expressed as means±standard errors of the mean. Colonization, inflammation, and behavioral data were analyzed with the Student t test or a Kruskal-Wallis test, followed by the Dunn post test, or with analysis of variance, followed by Dunnett's post test; Prism software, version 5 (GraphPad), was used, as appropriate.

Example 2

TLR4-Dependent Pain

NU14 Induction of Pain Specific to the Pelvic Area.

In experiments conducted during development of embodiments of the present invention, female C57BL/6J (B6) mice were instilled with $1 \times 10^8$ colony-forming units of *E. coli* into the bladder via transurethral catheter (Table 1). To assess tactile sensitivity, mice were stimulated with von Frey filaments. Mechanical stimulation of the pelvic area of saline-instilled mice resulted in a response frequency associated with the applied force, and this response profile did not change during the 14-day course of the experiment (FIGS. 1A and 1E). Similar to findings in saline-instilled mice, the response profile of 83972-infected mice did not change significantly during the 14-day course of the experiment (FIGS. 1B and 1E). In contrast, although NU14-infected mice exhibited the same baseline response as saline- and 83972-infected mice, the response to pelvic stimulation was significantly greater by day 1 after infection, peaked at day 2, and slowly declined but remained significantly elevated until day 10 (FIGS. 1C and 1E). There were no NU14-induced changes in tactile sensitivity of the plantar region of the hind paw or detectable weight changes. These data indicate that NU14 induces no changes in gross physiology and pain specific to the pelvic region.

Mast Cells and NU14-Induced Pelvic Pain.

Experiments conducted during development of embodiments of the present invention demonstrate that a mouse model of interstitial cystitis developed bladder-associated pelvic pain that is dependent on mast cells (17, herein incorporated by reference in its entirety). Mast cells have been shown to be important in defense from bacterial infection (28). To test whether mast cells play a role in NU14-induced pain, mast cell-deficient ($Kit^{W-sh}/Kit^{W-sh}$) mice were infected with NU14. Similar to NU14-infected B6 mice, NU14-infected $Kit^{W-sh}/Kit^{W-sh}$ mice exhibited responses to pelvic stimulation that were significantly greater by day 1 after infection, peaked at day 2, and remained significantly elevated until day 10 (FIGS. 1D and 1E). In contrast to the wild-type NU14-infected mice, NU14-infected $Kit^{W-sh}/Kit^{W-sh}$ mice exhibited a prolonged increase in pelvic sensitivity until day 7 (FIG. 1E), indicating that mast cells may help resolve the pelvic pain.

Organ Cross-Talk in UTI Associated Pelvic Pain.

Figure 2:
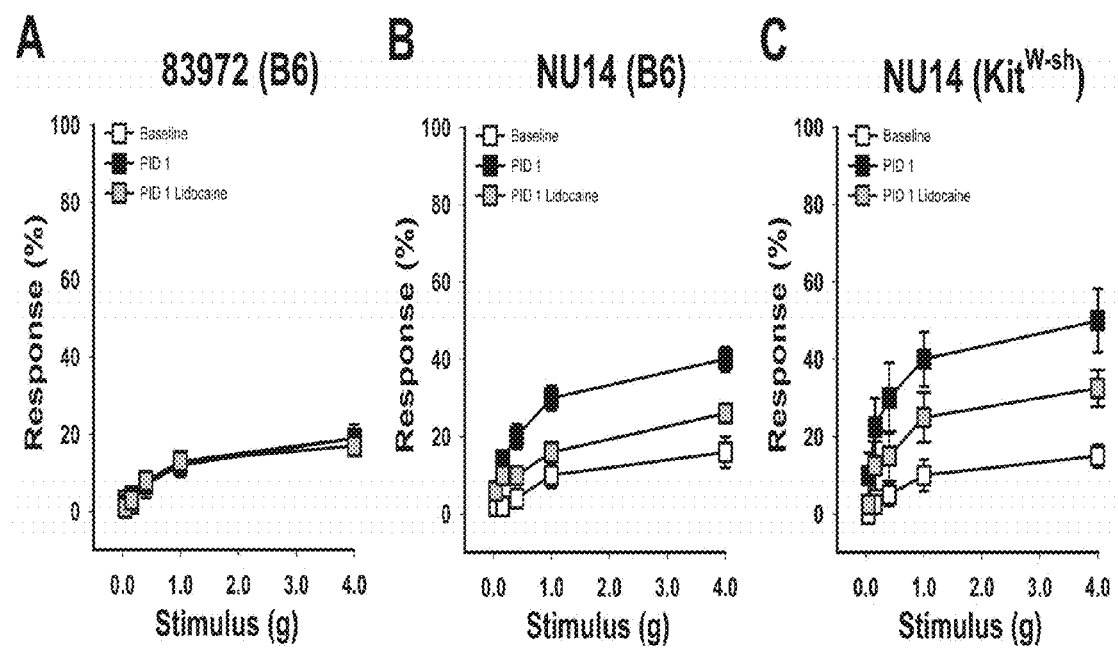
FIG. 2 shows graphs demonstrating that UTI-associated pelvic pain is attenuated by organ cross-talk. Modulation of referred visceral hyperalgesia by colonic lidocaine was measured as responses to mechanical stimulation of the pelvic region with von Frey filaments of 5 intensities. Responsiveness was characterized before infection (baseline), on postinfection day (PID) 1, and 45 min after colonic administration of 2% lidocaine on day 1. Instilling 50 µL of lidocaine into the colon of B6 mice; B) or mast cell-deficient Kit$^{W\text{-}sh}$ mice; C) reduced pelvic pain responses, whereas lidocaine had no significant effect on mice infected with 83972.

Instillation of 2% lidocaine directly into the colon attenuates bladder-induced pelvic pain in mice, demonstrating organ cross-talk in pelvic pain relief (18, herein incorporated by reference in its entirety). A similar strategy was used to determine whether NU14-induced pelvic pain was modulated by organ cross-talk. Lidocaine instilled into the colon significantly reduced the response to mechanical stimulation with von Frey filaments, by ~66% in wild-type infected mice (FIG. 2B) and ~56% in mast cell-deficient mice (FIG. 2C), whereas 83972 animals exhibited no loss of pelvic sensitivity after saline instillation (FIG. 2A). These data demonstrate that neurogenic cystitis and UTI-associated pelvic pain are similarly modulated by organ cross-talk.

NU14-Induced Pelvic Pain not Correlated with Bladder Colonization.

Figure 3:
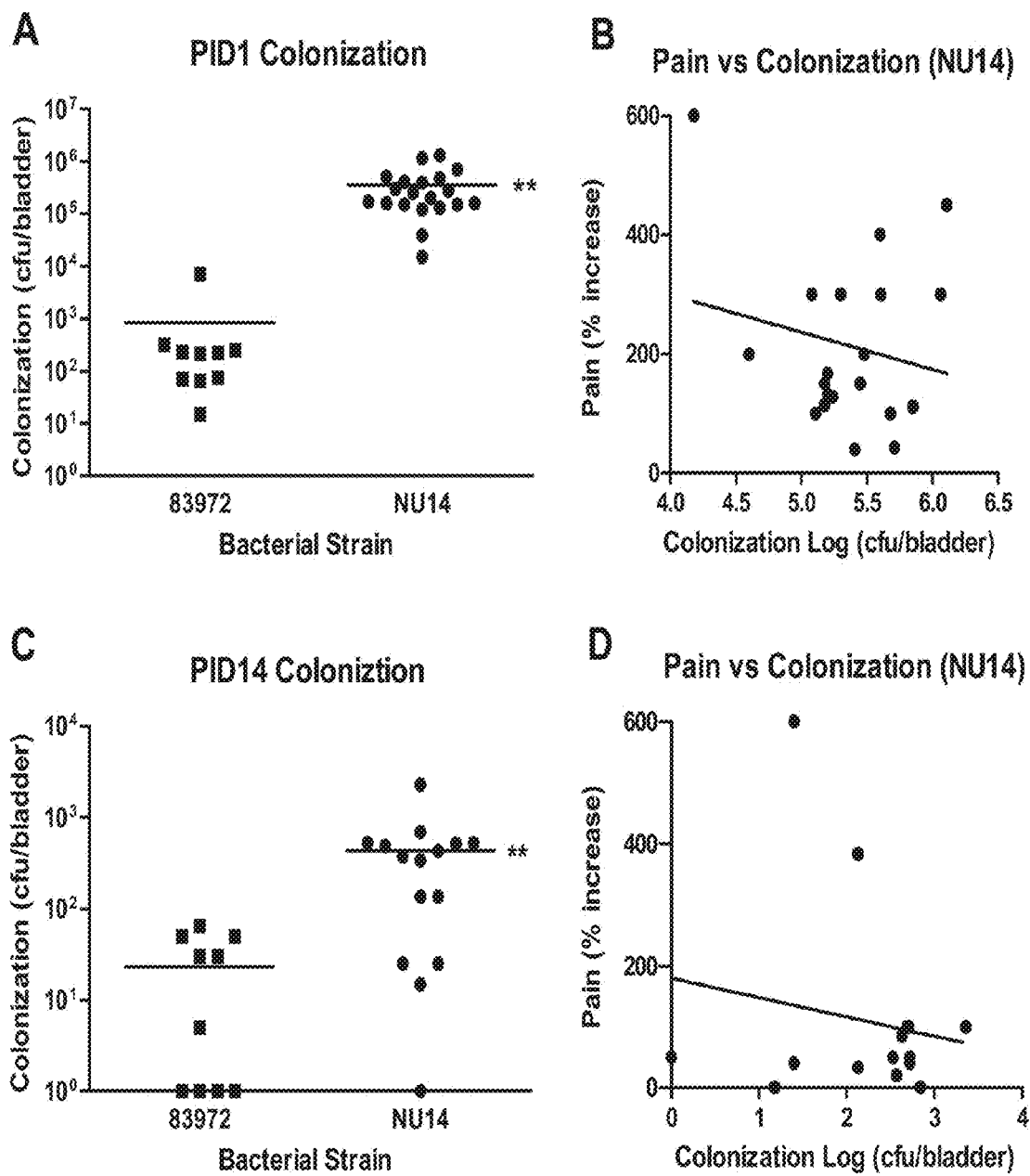
FIG. 3 shows graphs demonstrating that NU14-induced pelvic pain is not correlated with bacterial colonization of the bladder. Wild-type mice were infected with either 83972 or NU14, and bacterial colonization was measured 24 h or 14 days after infection. A and C, Both 83972 and NU14 colonized the bladder, but NU14 colonization was significantly greater than 83972 colonization at 24 h (A) and 14 days (C) after infection; cfu, colony-forming units; PID, postinfection day. Mean colonization levels are indicated by solid lines; bladder homogenates without detectable bacterial colonization appear on the x-axis. B and D, Pelvic pain was not correlated with bladder colonization at 24 h or 14 days after infection.

Mice were infected with either 83972 or NU14, and bacterial colonization was measured 24 h and 14 days after infection. Both 83972 and NU14 colonized the bladder, but NU14 colonization was significantly greater than 83972 colonization at 24 h and 14 days after infection (FIGS. 3A and 3C). However, pelvic pain was not correlated with bladder colonization at 24 h (FIG. 3B) or 14 days (FIG. 3D) after infection.

Type 1 Pilus Status and UTI-Associated Pelvic Pain.

A difference between NU14 and 83972 strains is that NU14 bacteria express type 1 pili on their surface, whereas 83972 bacteria are not piliated (Table 1). Pilus expression was varied for NU14 and 83972 bacteria (Table 1), instilled these bacteria into the bladder of B6 mice, and then assessed pain responses. Before instillation, a hemagglutination assay was performed on each bacterial strain tested to confirm the presence or absence of type 1 pili. We found that endowing 83972 with functional type 1 pilus expression did not induce significant pelvic pain (FIGS. 4A-C and 4F). In contrast, both NU14 ($fimH^+$) and NU14-1 ($fimH^-$) induced significant pelvic pain in infected mice (FIG. 4D-F). These data demonstrate that type 1 pilus status does not influence UTI-associated pelvic pain, indicating that pain is initiated by other bacterial factors.

NU14-Induced Pelvic Pain not Correlated with Bladder Inflammation.

Figure 5:
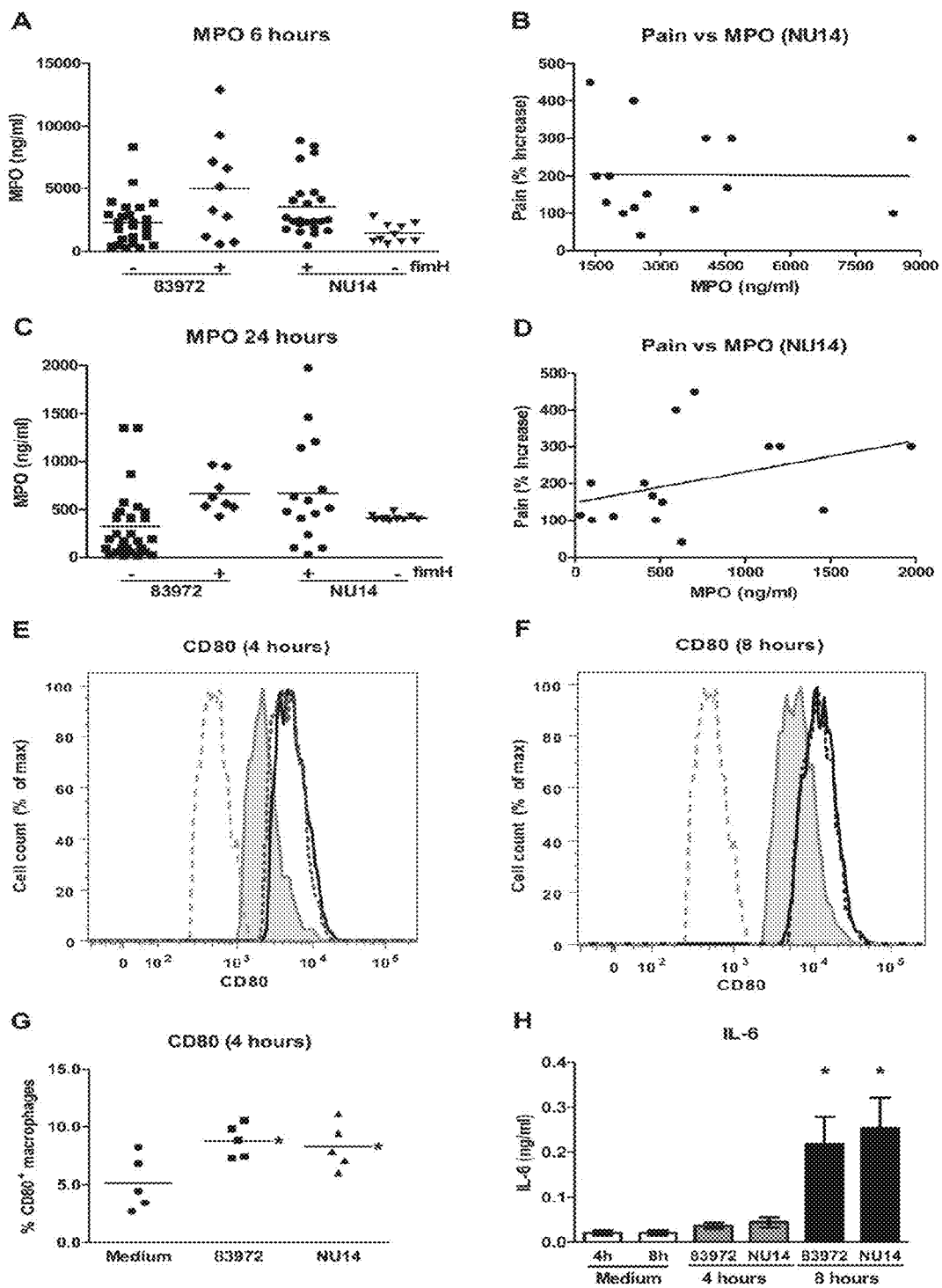
FIG. 5 shows graphs demonstrating that NU14-induced pelvic pain is not correlated with urine neutrophil myeloperoxidase (MPO). Female B6 mice were infected with 83972, 83972:pGB4, NU14, or NU14-1, and neutrophil MPO, a measure of inflammation was quantified 6 h or 24 h after infection. A, NU14-1 MPO levels are significantly lower than those for both NU14 and 83972:pGB4 6 h after infection, with no other statistically significant differences between any groups. C, NU14-1 MPO levels were significantly lower than those for 83972:pGB4, and NU14 MPO levels were significantly higher than those for 83972 24 h after infection, with no other statistically significant differences between any groups C. B and D, Mean MPO levels are indicated by solid lines. Pelvic pain was not correlated with MPO levels at 6 h or 24 h after infection. E and F, Histograms of CD80$^+$ cells 4 h (E) and 8 h (F) after lipopolysaccharide (LPS) stimulation. Solid gray line with shading, medium; dashed line, isotype control; dotted black line, 83972; solid black line, NU14. G, Both NU14 and 83972 LPS significantly increased numbers of CD80$^+$ macrophages compared with medium. H, Both NU14 and 83972 LPS induced significantly increased levels of interleukin (IL)-6.

MPO was quantified as a marker of inflammation in the murine UTI model (29). MPO was also quantified to determine whether pelvic pain correlated directly with inflammation. Mice were infected with either 83972 or NU14, and MPO levels in the urine were measured 6 or 24 h after infection. MPO was not significantly different between 83972- and NU14-infected mice at 6 or 24 h after infection (FIGS. 5A and 5C, respectively). Pelvic pain was not correlated with MPO levels at 6 h (FIG. 5B) or 24 h (FIG. 5D) after infection. Furthermore, in primary cultures of macrophages, both NU14 and 83972 LPS induced similar significant increases in $CD80^+$ cells at 4 h (FIGS. 5E and 5G), with recovery by 8 h (FIG. 5F), whereas IL-6 supernatant levels were significantly elevated only at 8 h (FIG. 5H). In contrast, $CD86^+$ cell numbers were unchanged at either 4 or 8 h after NU14 or 83972 LPS application, compared with medium.

Induction of Pelvic Pain by NU14 LPS.

Figure 6:
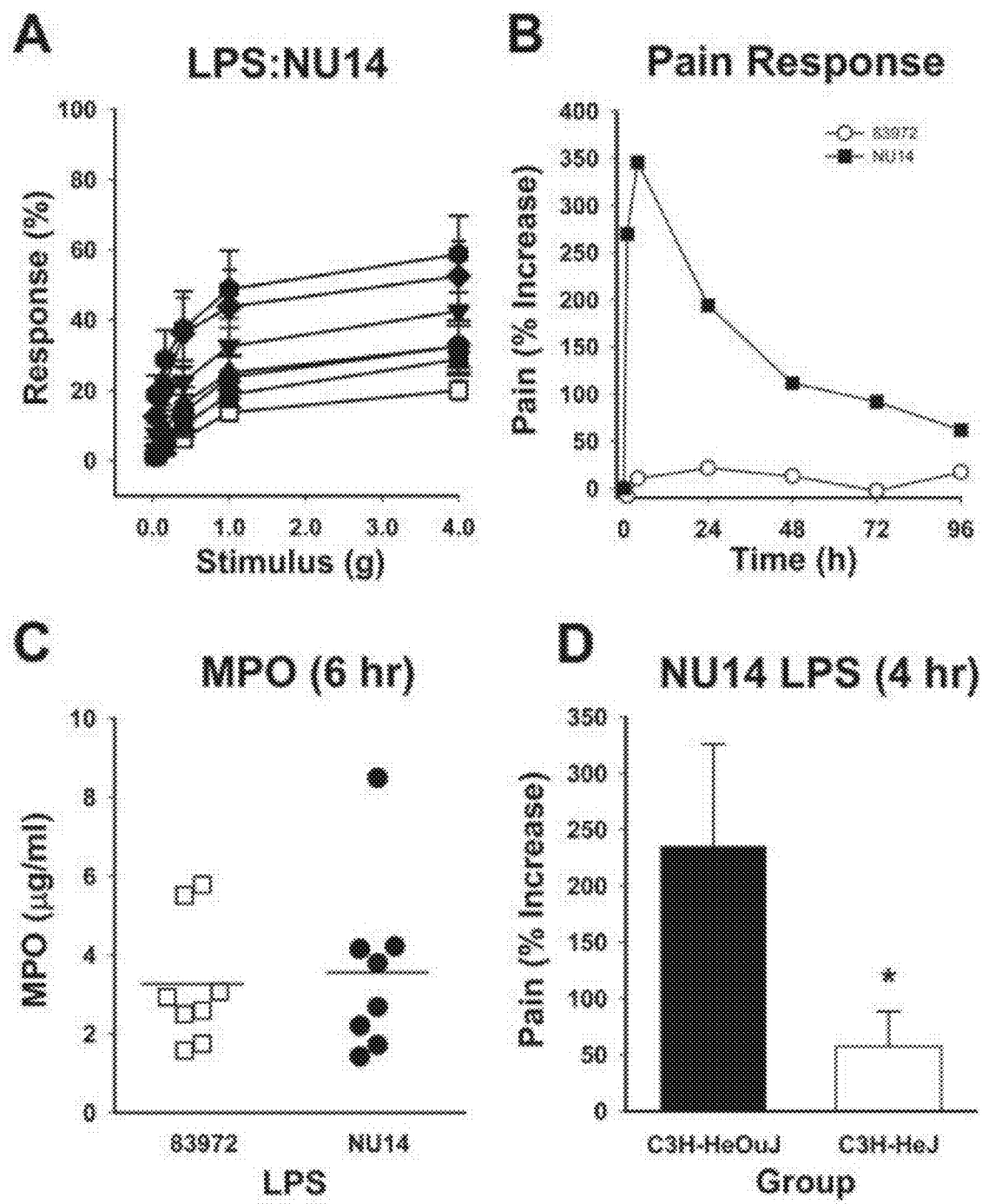
FIG. 6 shows graphs demonstrating that lipopolysaccharide (LPS) induces pelvic pain and represents a therapeutic target for pain relief. Referred visceral hyperalgesia was measured as responses to mechanical stimulation of the pelvic region with von Frey filaments of 5 intensities. Responsiveness was characterized at baseline and 1, 4, 24, 48, 72, and 96 h after 83972 or NU14 LPS instillation. A, Responses to pelvic stimulation of female B6 mice instilled with NU14 LPS. Analysis of variance indicated a significant increase in response frequency from baseline for all filaments tested in NU14 LPS-treated mice at 1, 4, and 24 h after instillation, with no significant differences in baseline between 83972- and NU14-treated mice. B, Percentage responses 1, 4, 24, 48, 72, and 96 h after instillation were calculated as total responses to all fibers relative to baseline responses for 83972 or NU14 LPS-instilled mice. C, LPS-induced myeloperoxidase (MPO) levels in 83972 and NU14 LPS-instilled mice. D, C3H-HeJ mice instilled with NU14 LPS exhibited a significant reduction in pelvic pain compared with C3H-HeOuJ mice instilled with NU14 LPS. Percentage responses 4 h after instillation were calculated as total responses to all fibers relative to baseline responses. E, Left panel is a cartoon and experimental timeline (intervention, saline or 83972 LPS). Right panel is a graph of the percentage responses at 1, 2, 3, 4, 5, and 6 days after NU14 instillation, calculated as total responses to all fibers relative to baseline responses for all groups of mice.

Studies have shown that when LPS was injected intraperitoneally or into the footpad of rats it produced hyperalgesia (30, 31, herein incorporated by reference in their entireties), and LPS has been shown to be important in bacteria-induced bladder inflammation (32, 33, herein incorporated by reference in their entireties). LPS was purified from 83972 or NU14 and instilled directly into the bladder of female B6 mice. The response profile of 83972 LPS-instilled mice did not change during the 4-day course of the experiment (FIG. 6B). In contrast, the response to pelvic stimulation was significantly greater 1 h after NU14 LPS instillation, peaking at 4 h after instillation and declining to baseline levels by 96 h after instillation (FIGS. 6A and 6B). Furthermore, levels of urinary MPO 6 h after instillation did not differ significantly between 83972 and NU14 LPS-instilled mice (FIG. 6C). These data suggest that NU14 LPS is capable of inducing pelvic pain independent of neutrophil-induced inflammation.

LPS acts through TLR4, and TLR4 is expressed on nociceptive neurons (34, herein incorporated by reference in its entirety). TLR4-deficient C3H-HeJ and the isogenic wild-type C3H-HeOuJ mouse strain was used to determine if NU14 LPS induces pelvic pain through TLR4. C3H-HeJ mice exhibited significantly reduced pelvic pain compared with the C3H-HeOuJ mice 4 h after instillation of NU14 LPS (FIG. 6D). These data indicate that NU14 LPS is acting through TLR4 to initiate NU14-induced pelvic pain.

83972 LPS did not cause pelvic pain. B6 mice were instilled with NU14 bacteria and then instilled with saline 24 h later; Saline instillation did not alter the development of significant pelvic pain (FIG. 6E). Similarly, mice instilled with both NU14 bacteria and 83972 LPS and then instilled with saline 24 h later also developed significant pelvic pain. In contrast to these groups, mice instilled with NU14 bacteria and then instilled with 83972 LPS 24 h later exhibited a 40% reduction in NU14-induced pelvic pain 24 h after instillation of 83972 LPS (FIG. 6F). These data indicate that 83972 LPS acts as a TLR4 antagonist to attenuate UTI-induced pelvic pain.

Example 3

83972-Induced Analgesia

This example describes the analgesic activity of 83972 *E. coli*.

Figure 7:
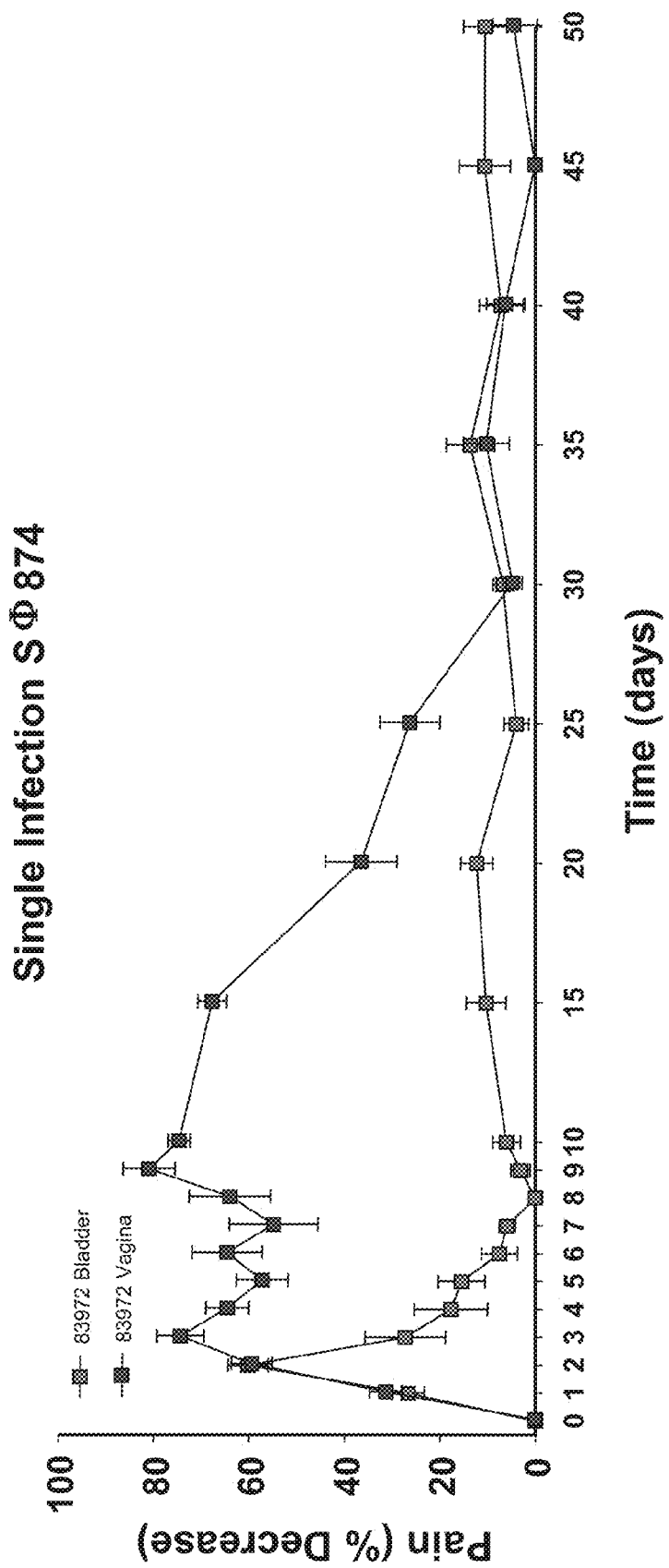
FIG. 7 shows that SΦ874-induced chronic pelvic pain is differentially attenuated by 83972.

Experiments were conducted to show the benefit of 83972 against pain caused by transient SF874 infection. 83972 was administered at 20 days after SF874 infection. Results are shown in FIG. 7. Vaginal 83972 administration confers long-lasting relief, whereas bladder administration yields only transient benefit. A single infection with SF874 was sufficient to induce pain for weeks—equivalent to >6 yrs in a human.

Figure 8:
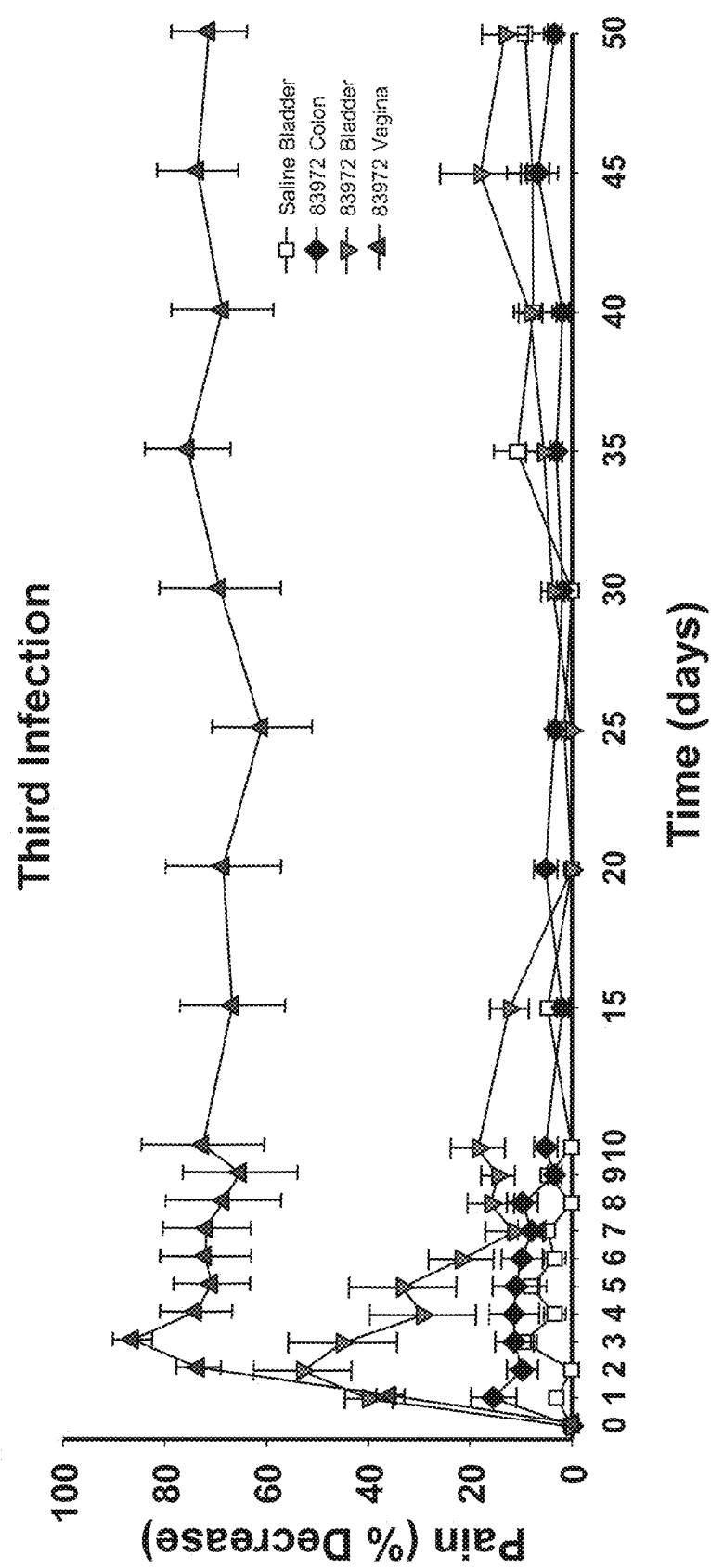
FIG. 8 shows that ΔwaaL-induced chronic pelvic pain is differentially attenuated by 83972.

Additional experiments were conducted to show the benefit of 83972 on pain caused experiments by DwaaL. DwaaL induces "adaptive chronic" pain upon a second and third serial infection. 83972 was administered at 14 days after a $3^{rd}$ DwaaL infection. Results are shown in FIG. 8. 83972 suppresses pain transiently (bladder) or durably (vagina), depending upon site of administration.

Figure 9:
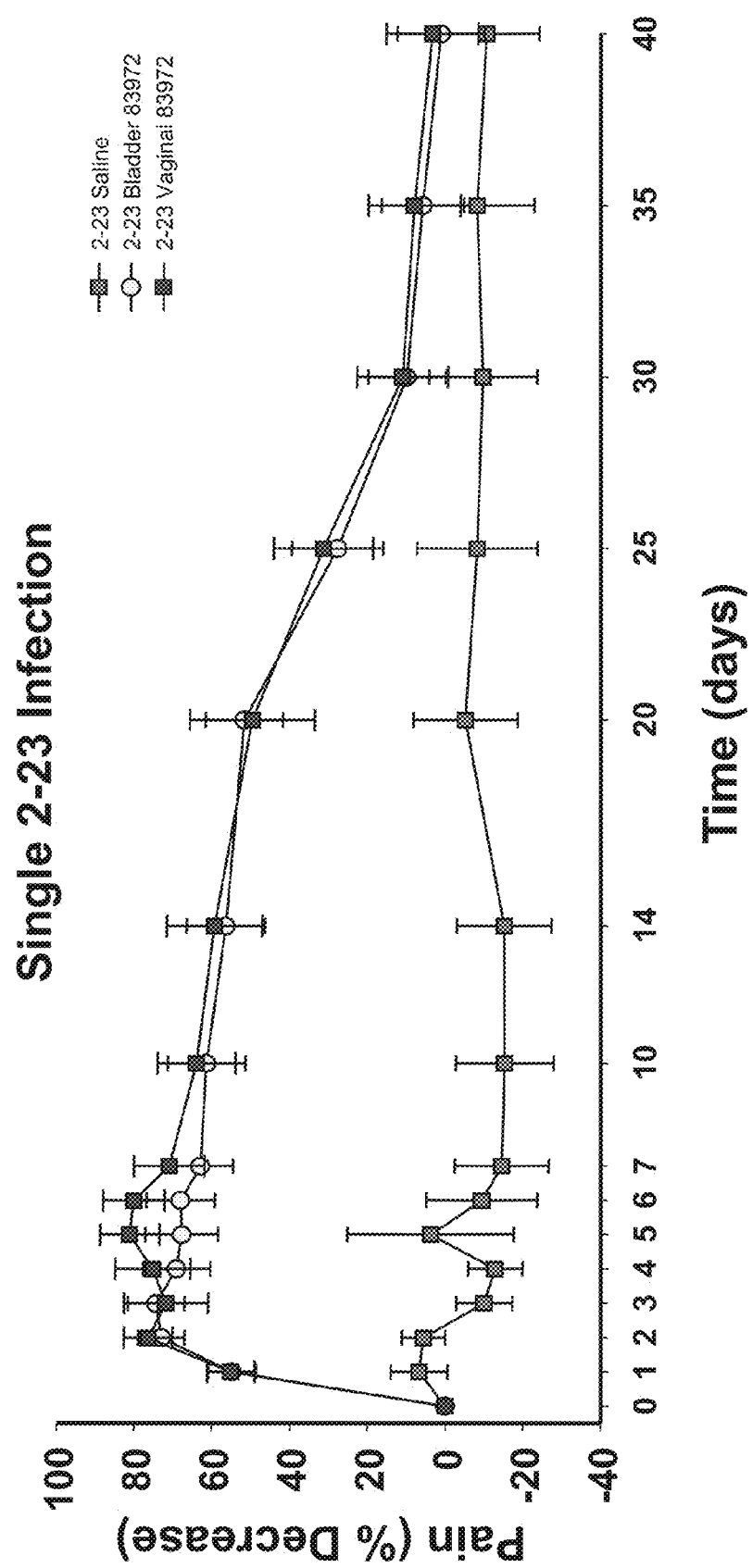
FIG. 9 shows that 2-23-induced chronic pelvic pain is attenuated by 83972.
Figure 10:
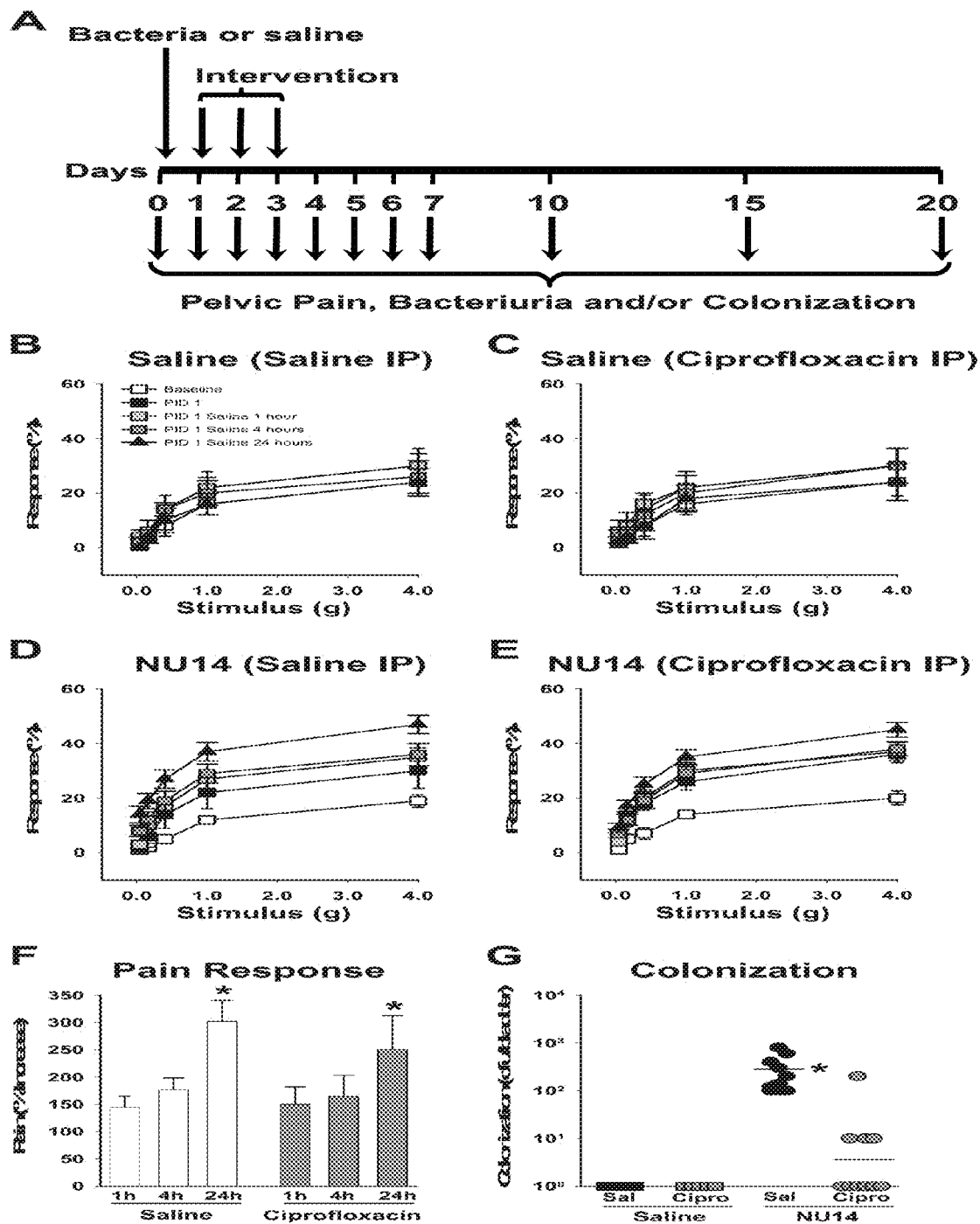
FIG. 10 shows response to NU14 induced pain with and without antibiotics. A. Study overview. B. Response to saline. C. Response to Ciprofloxacin. D. Response to NU14. E. Response to NU14 plus Ciprofloxacin. F. Pain response in the presence of saline or Ciprofloxacin. G. Colonization of NU14 in the presence of saline or Ciprofloxacin.
Figure 11:
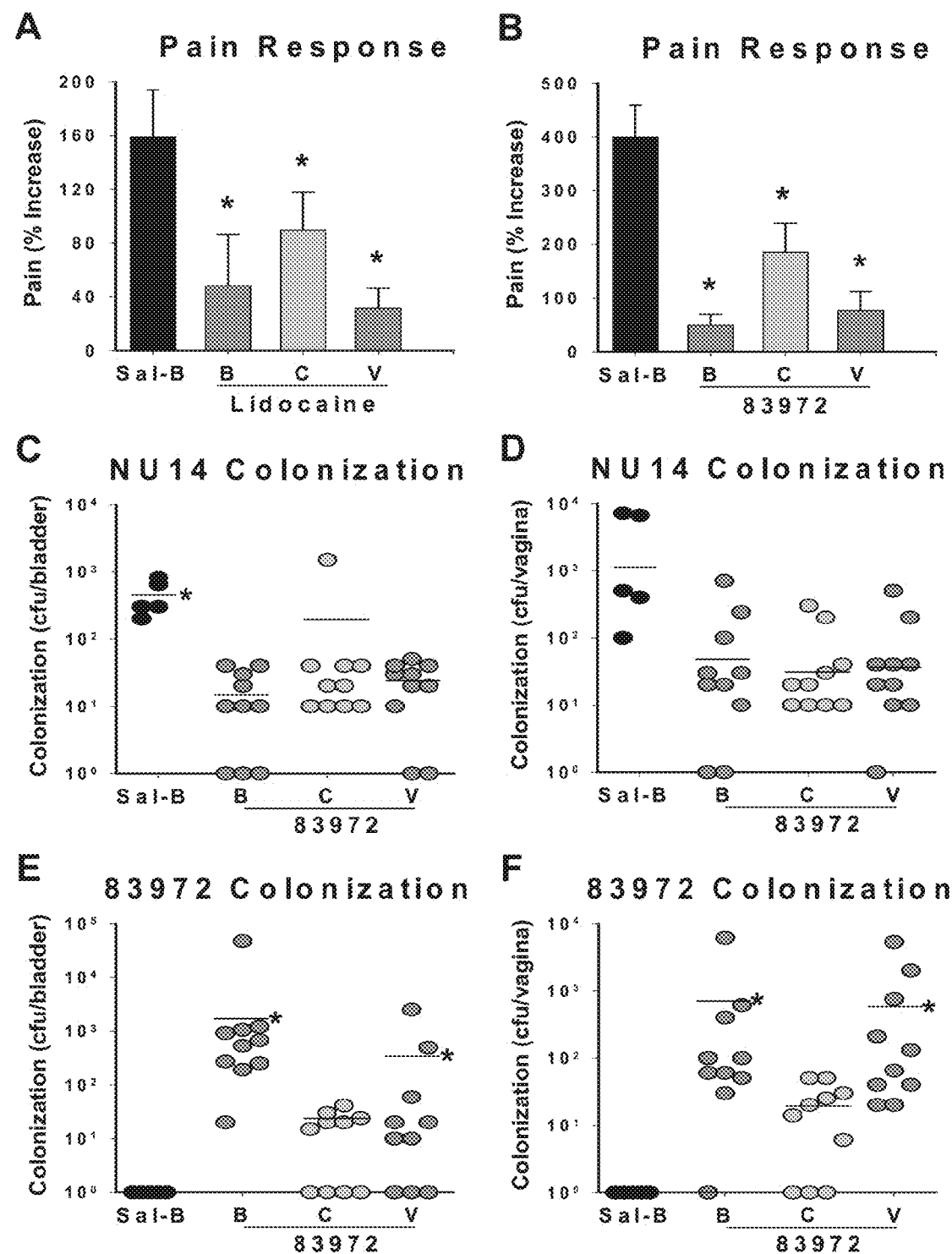
FIG. 11 shows pain response and colonization of NU14 and the presence and absence of 83972. Pain response in presence of lidocaine (A) or 83972 (B). C and D. NU14 colonization in the presence of 83972 or saline in the bladder (C) or vagina (D). E and F. 83972 colonization in the bladder (E) or vagina (F).
Figure 13:
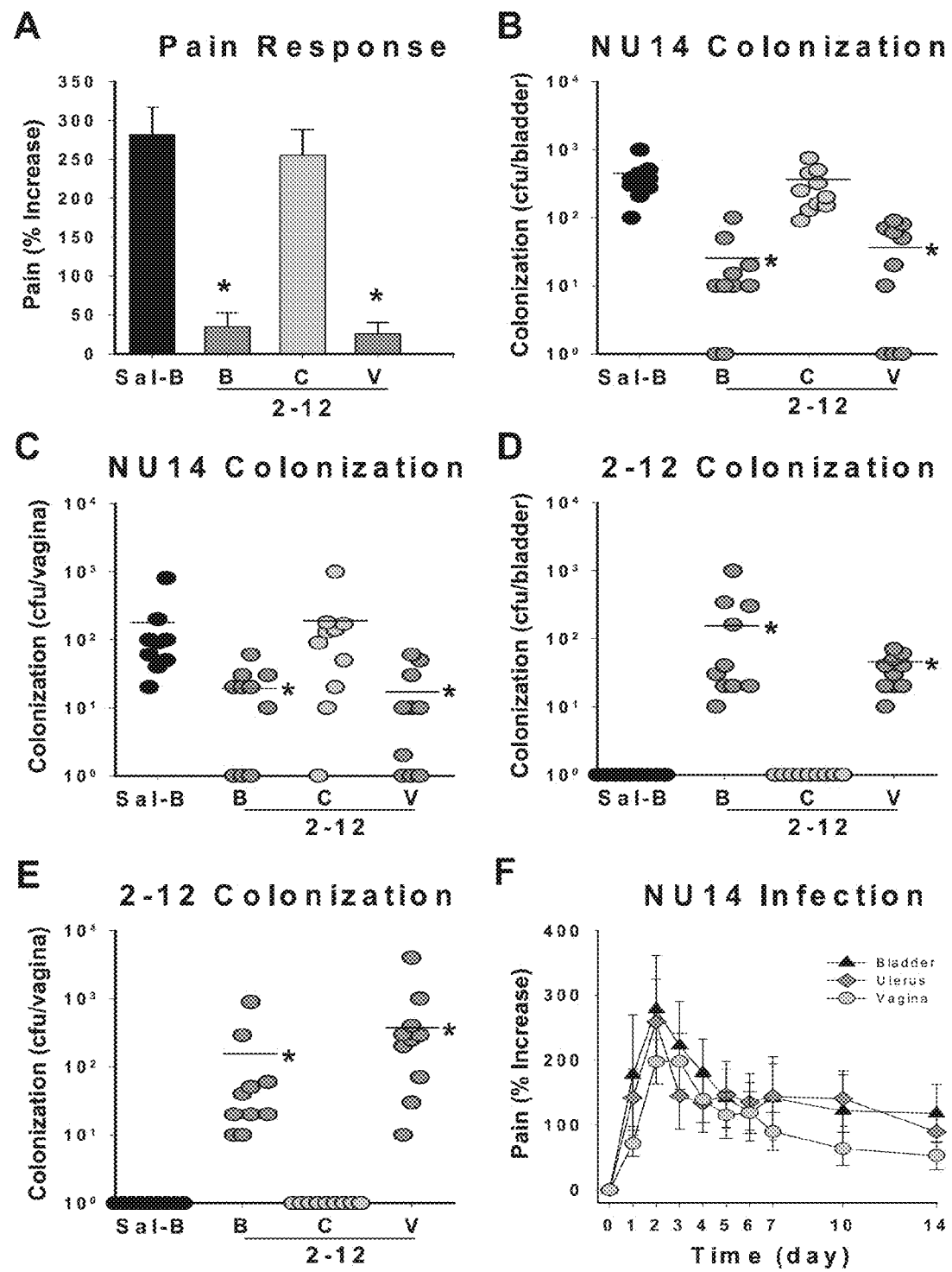
FIG. 13 shows pain response and colonization of NU14 with 2-12.
Figure 14:
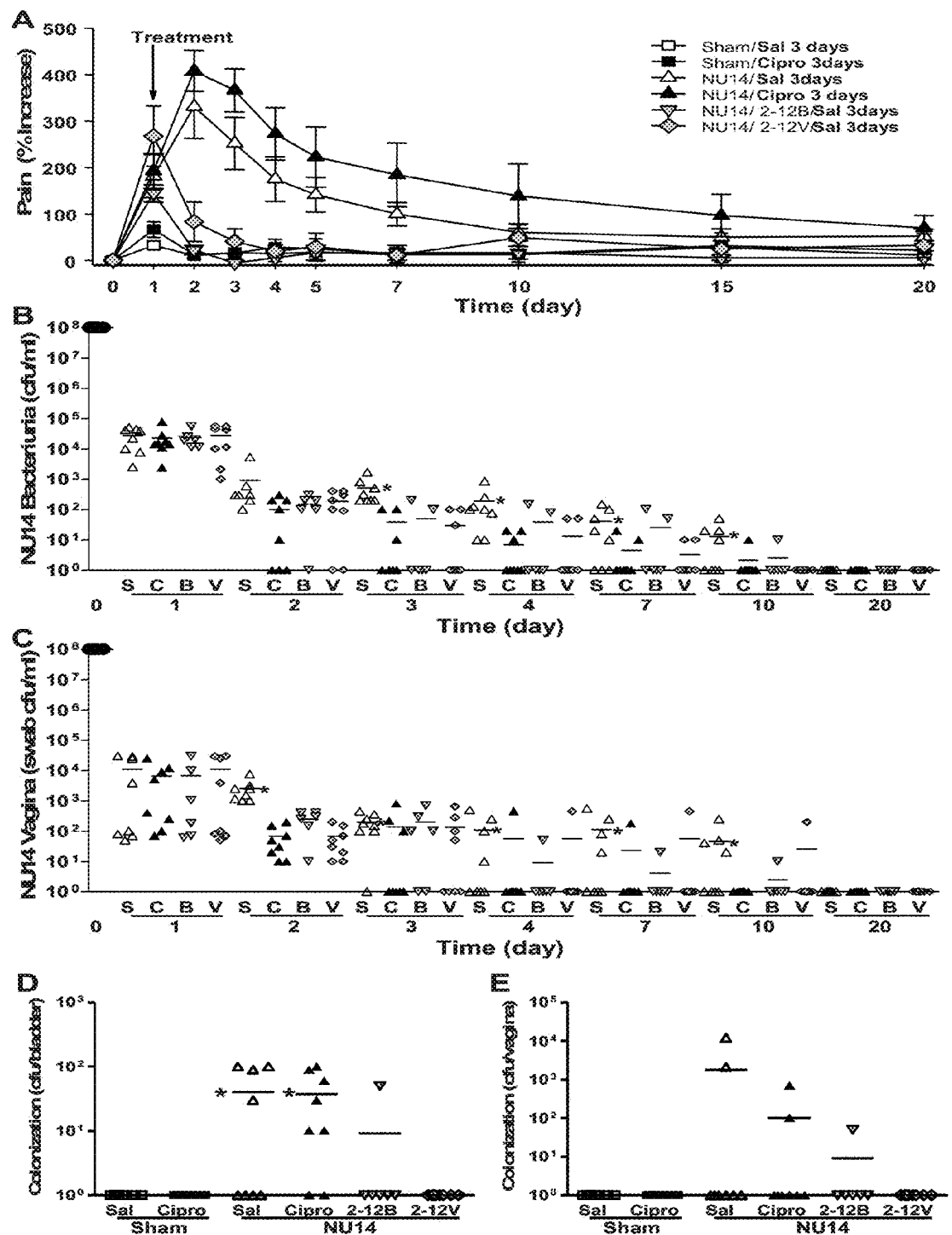
FIG. 14 shows treatment with antibiotics and 2-12.
Figure 15:
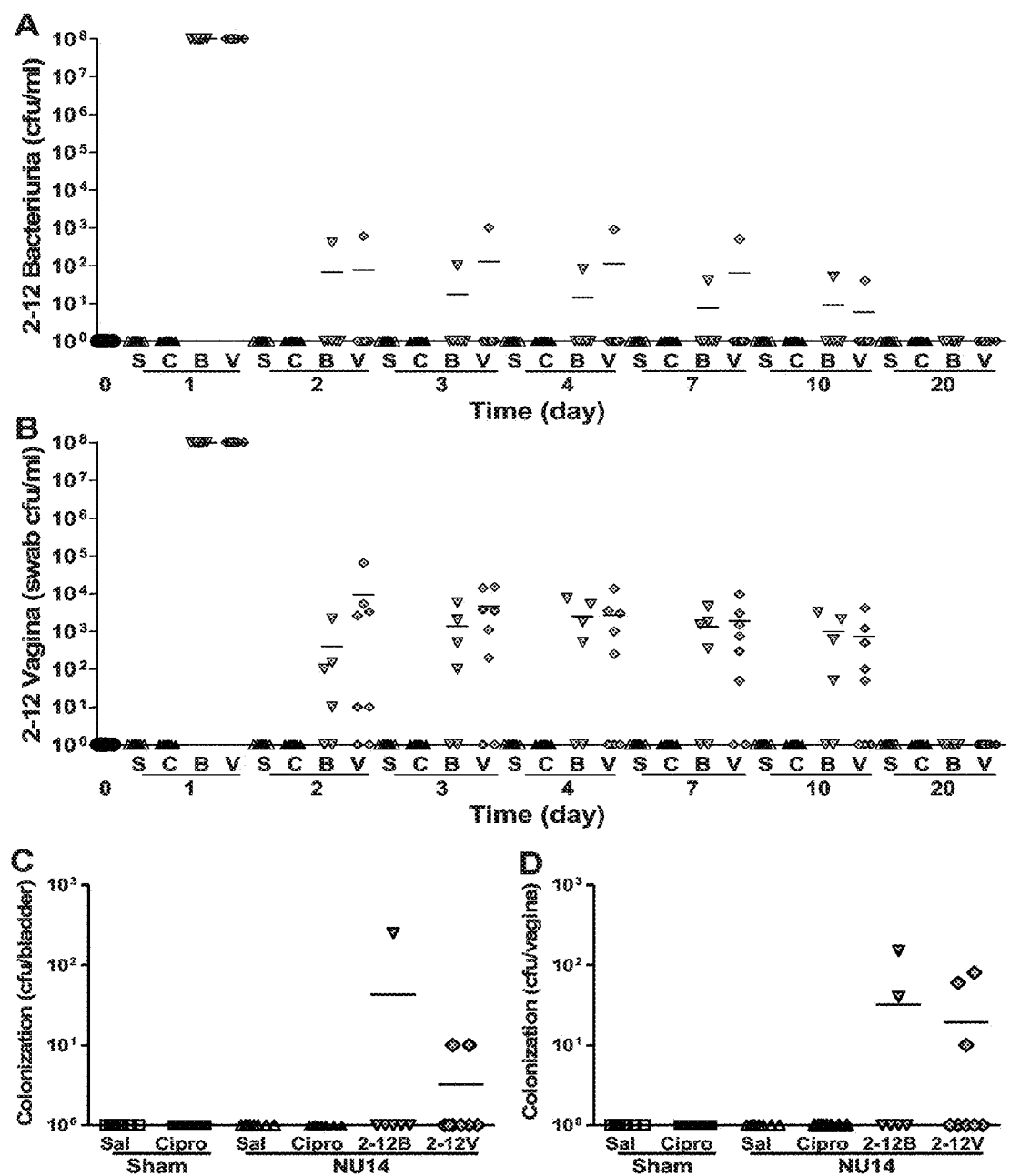
FIG. 15 shows treatment with antibiotics and 2-12. A. Pain response in the presence of saline or 2-12 over time. B and C. NU14 colonization in the presence of saline or 2-12. D and e. 2-12 colonization in the presence of saline or 2-12. F. NU14 infection timecourse.
Figure 16:
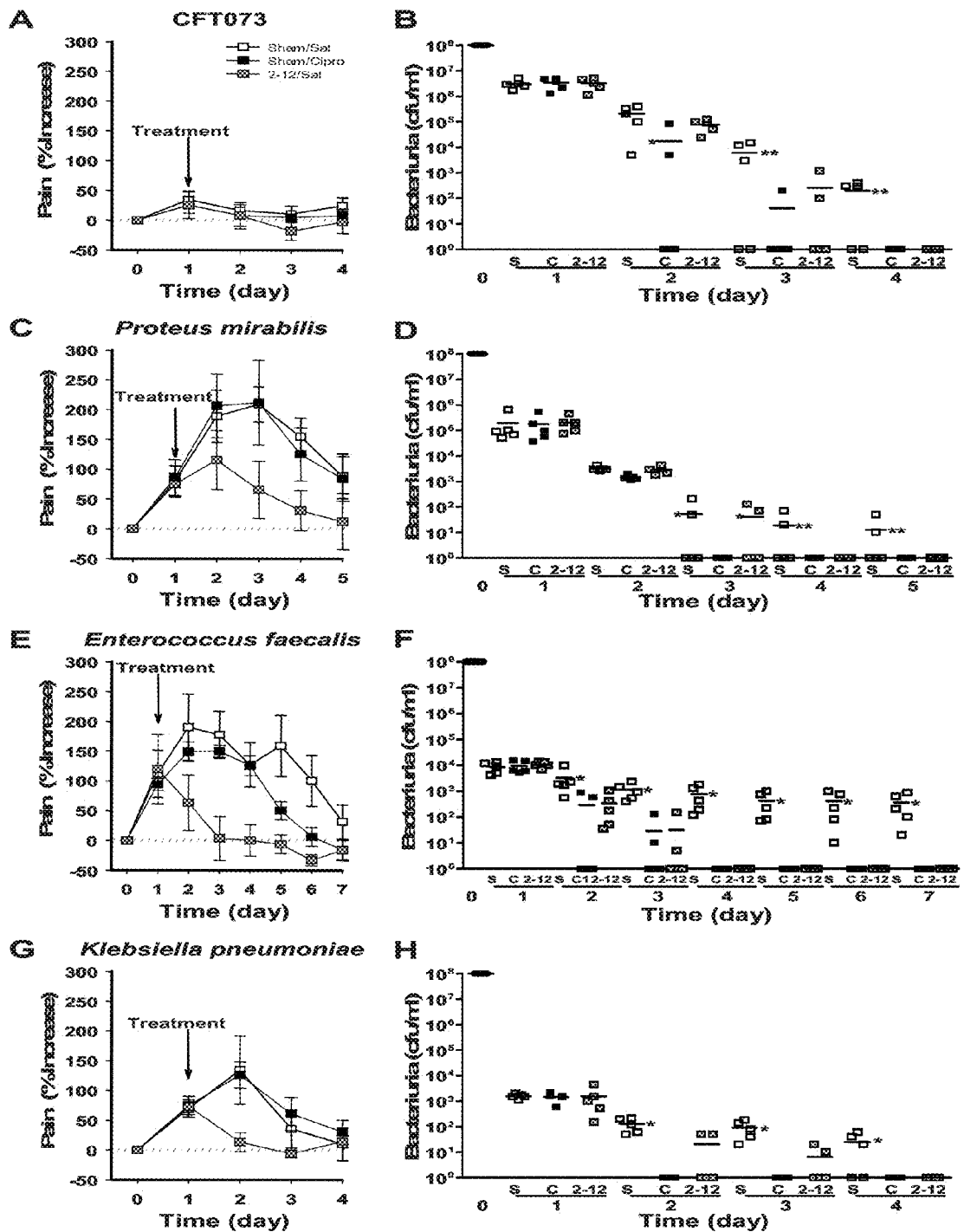
FIG. 16 shows treatment with antibiotic and 2-12. A. Pain response over time. B. NU14 colonization over time. D. Colonization in the presence of control or NU14 over time.
Figure 17:
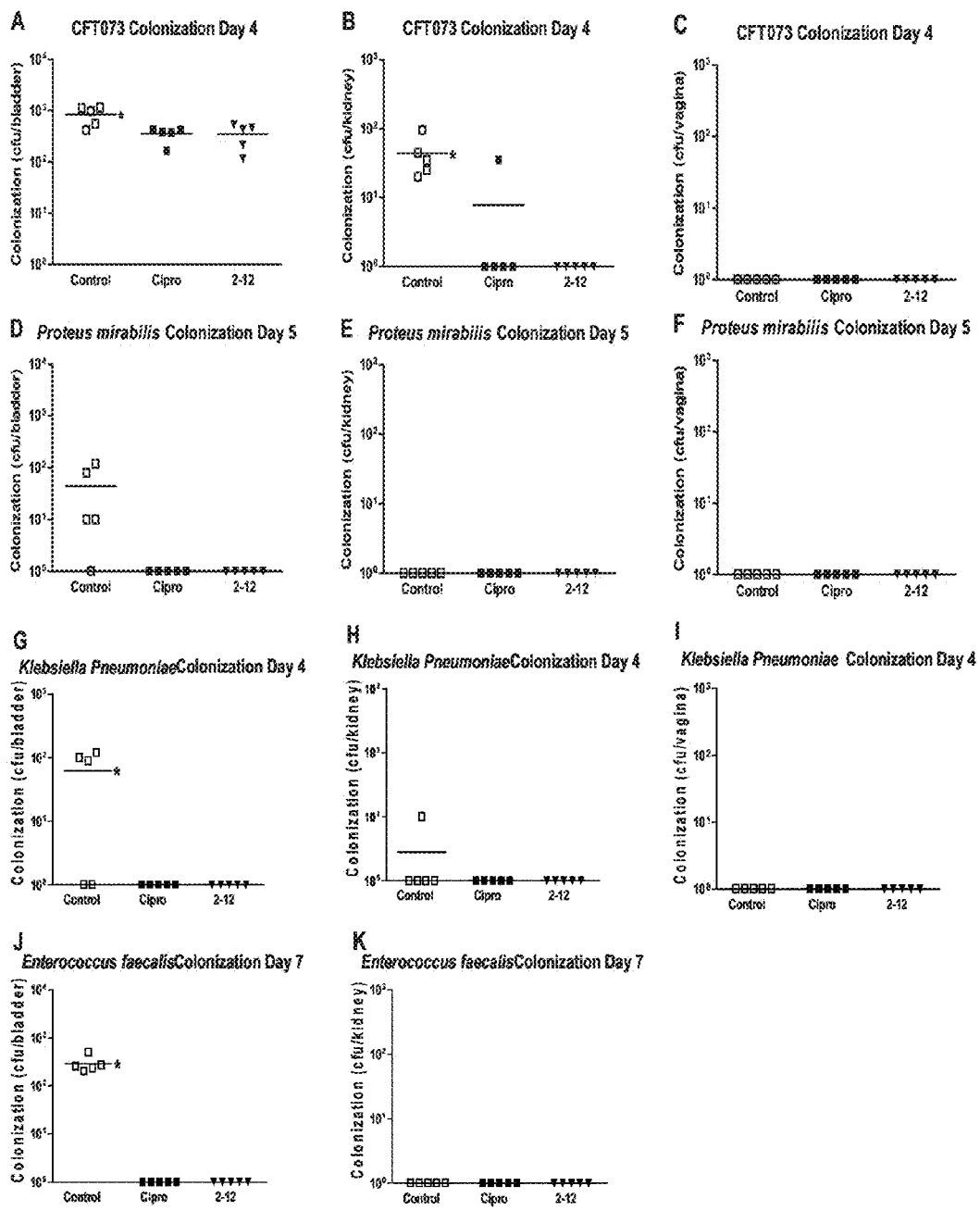
FIG. 17 shows that 2-12 is antimicrobial against UPEC pyelonephritis (B) and bladder *Proteus/Kleb/E.faec* (D). A. 2-12 colonization. C. Colonization in the presence of control or NU14.
Figure 19:
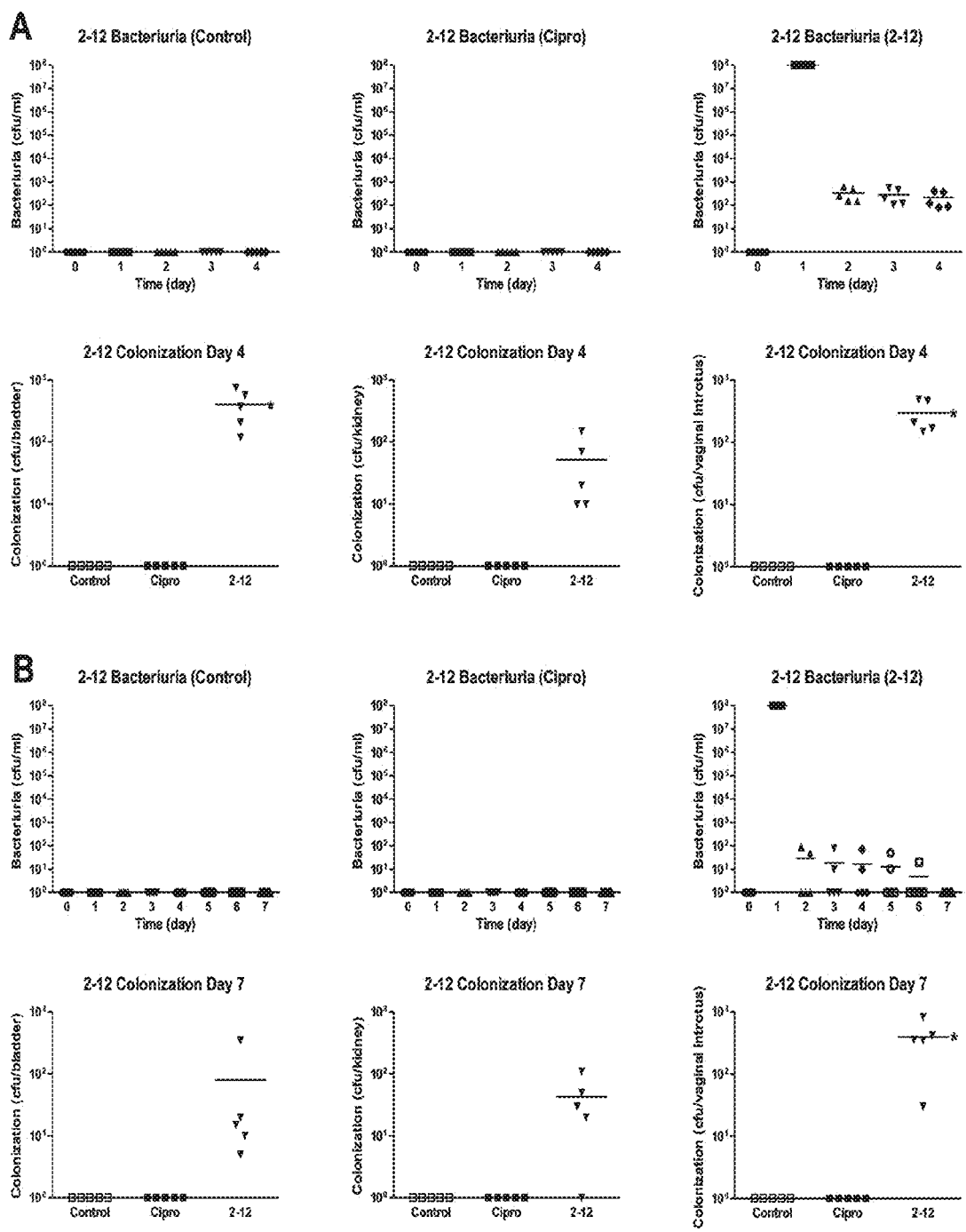
FIG. 19 shows 2-12 colonization (Saline, Cipro, 2-12). A) *Klebsiella* B) *E. faecalis*.

Experiments were conducted to show the benefit of 83972 on pain caused by 2-23. 2-23 is a clinical strain isolated from a cystitis patient, and it induces chronic pain in mice that lasts the equivalent of several human years. 83972 was administered at 60 days after SF874 infection. Results are shown in FIG. 9. 83972 brings long-lasting relief.

Example 4

2-12-Induced Analgesia

This example describes the analgesic activity of 2-12 *E. coli*.

A variety of probiotic *E. coli* strains were compared to Ciprofloxin in their ability to reduce pain caused by a variety of pathogenic *E. coli* strains. Results are shown in FIGS. 10-19. The results indicate that ASB strain 2-12 has attributes including analgesic effects, antimicrobial activity, and effects that are applicable to UTI by UPEC as well as UTI by other uropathogens.

Example 5

Probiotics

Figure 20:
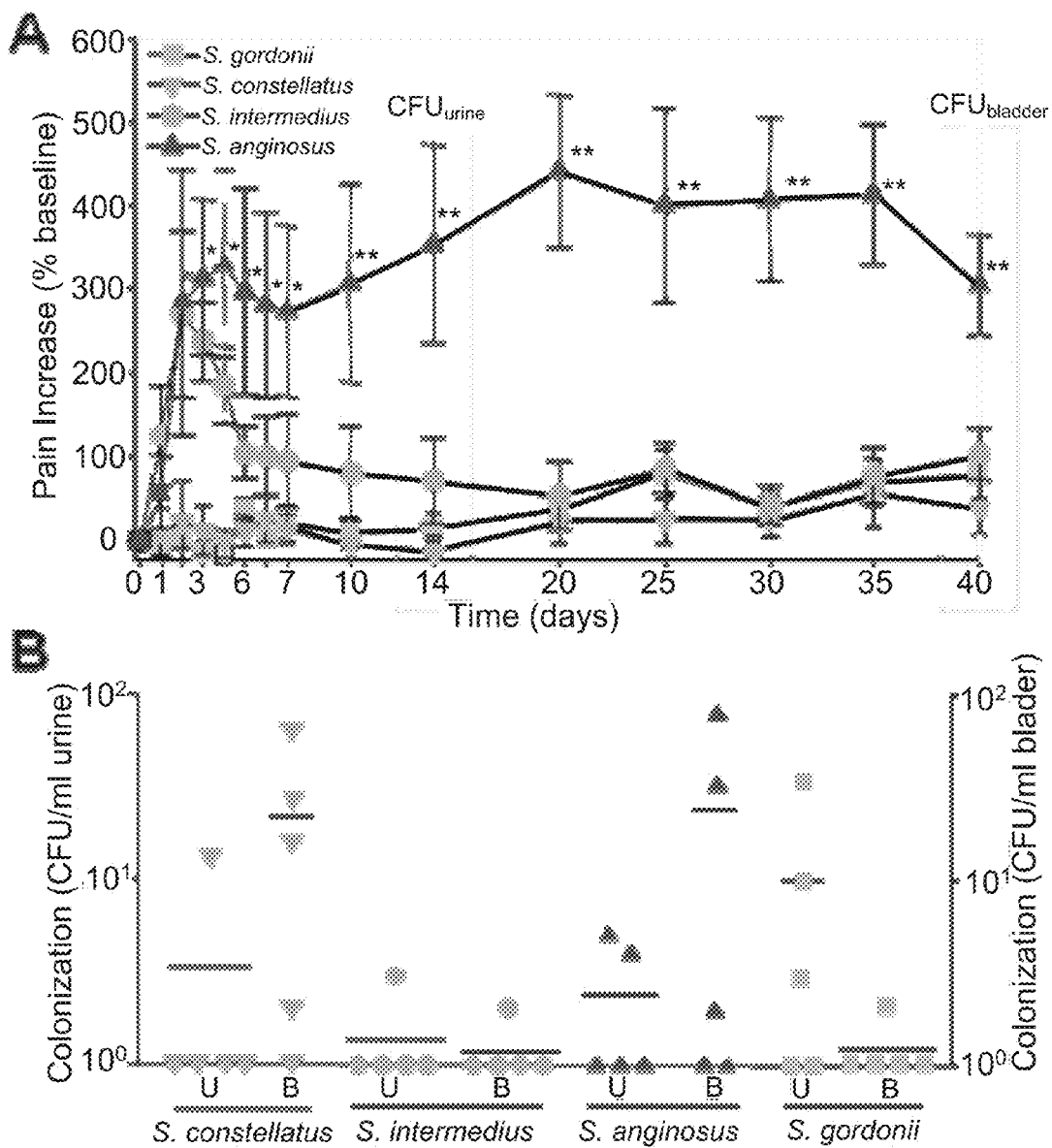
FIG. 20 shows that oral Streptococci induce differential pain states independent of colonization. A) Bladder instillation of $10^8$ CFU *S. anginosus* caused chronic pain that was significant from baseline (P<0.05*) by Day 2 and significant from *S. intermedius* by Day 10 (P<0.05**; n=5). *S. gordonii* and *constellatus* induced no pain response. B) Most urines (U) and bladders (B) were sterile at Day 14 and Day 40, respectively, with no correlation with pain.
Figure 21:
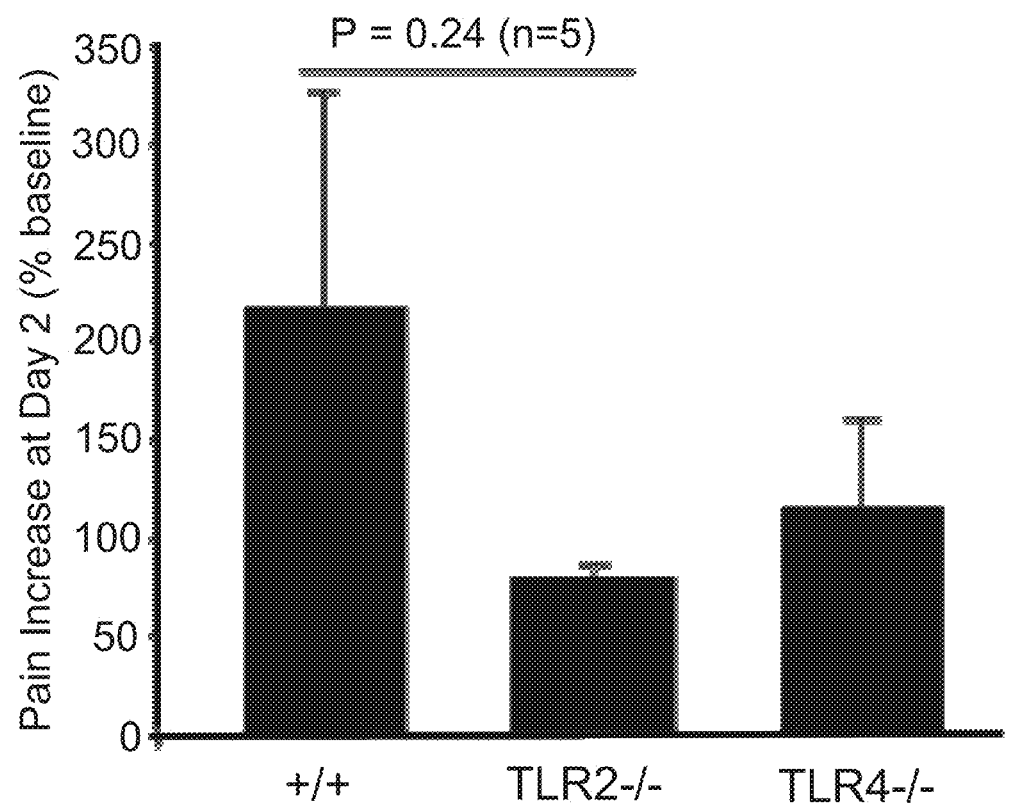
FIG. 21 shows that TLRs mediate *S. milleri* pain. Mice (n=5) were instilled with *S. anginosis* via catheter, and pelvic pain responses were quantified at Day 2. TLR2−/− mice and TLR4−/− mice showed responses reduced by 64% and 47%, respectively (P=0.24 and P=0.41).

This example describes strains of *Streptococcus*. Results are shown in FIGS. 20-21 and show that different strains can induce acute, chronic, or null pain (asymptomatic) responses. FIG. 20 shows that oral Streptococci induce differential pain states independent of colonization. A) Bladder instillation of $10^8$ CFU *S. anginosus* caused chronic pain that was significant from baseline (P<0.05*) by Day 2 and significant from *S. intermedius* by Day 10 (P<0.05**; n=5). *S. gordonii* and *constellatus* induced no pain response. B) Most urines (U) and bladders (B) were sterile at Day 14 and Day 40, respectively, with no correlation with pain.

FIG. 21 shows that TLRs mediate *S. milleri* pain. Mice (n=5) were instilled with *S. anginosis* via catheter, and pelvic pain responses were quantified at Day 2. TLR2−/− mice and TLR4−/− mice showed responses reduced by 64% and 47%, respectively (P=0.24 and P=0.41).

All publications and patents cited in the present application and listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for treating or reducing the probability of developing pelvic pain comprising, administering a probiotic composition comprising a strain of *E. coli* deposited with the American Type Culture Collection under Accession Number PTA-124177 to a subject having pelvic pain or at risk of pelvic pain.

2. The method of claim 1, wherein said pain is due to an active or past urinary tract infection.

3. The method of claim 1, wherein said subject has been diagnosed with a urinary tract infection.

4. The method of claim 1, wherein said probiotic composition comprises LPS.

5. The method of claim 1, wherein said probiotic composition treats or prevents infection and/or inflammation in addition to pain.

6. The method of claim 1, wherein said probiotic composition is administered as a tablet, capsule, pill, cream, ointment, lotion, salve, balm, suppository, solution, elixir, syrup, suspension, lozenge, paste or spray.

7. The method of claim 1, wherein said probiotic composition is administered systemically.

8. The method of claim 1, wherein said probiotic composition is administered locally to the region of infection and/or pain.

9. The method of claim 1, wherein said probiotic composition is administered vaginally.

10. The method of claim 1, wherein said probiotic composition is administered such that pain is treated via organ crosstalk.

* * * * *